US008682692B2

(12) United States Patent
Morris

(10) Patent No.: US 8,682,692 B2
(45) Date of Patent: *Mar. 25, 2014

(54) MEDICAL INFORMATION HANDLING METHOD

(75) Inventor: Tommy J. Morris, New Market, MD (US)

(73) Assignee: The United States of America as Represented by the Secretary of the Army, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/620,045

(22) Filed: Sep. 14, 2012

(65) Prior Publication Data

US 2013/0013342 A1    Jan. 10, 2013

Related U.S. Application Data

(60) Division of application No. 13/009,372, filed on Jan. 19, 2011, which is a continuation of application No. 10/438,327, filed on May 15, 2003, now Pat. No. 7,899,687.

(60) Provisional application No. 60/381,058, filed on May 15, 2002.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......................................................... 705/2–3
See application file for complete search history.

(56) References Cited

U.S. PATENT DOCUMENTS

| 3,872,448 | A | 3/1975 | Mitchell, Jr. |
| 4,839,822 | A | 6/1989 | Dormond et al. |
| 4,878,175 | A | 10/1989 | Norden-Paul et al. |
| 4,945,476 | A | 7/1990 | Bodick et al. |
| 5,065,315 | A | 11/1991 | Garcia |
| 5,077,666 | A | 12/1991 | Brimm et al. |
| 5,247,611 | A | 9/1993 | Norden-Paul et al. |
| 5,253,361 | A | 10/1993 | Thurman et al. |
| 5,253,362 | A | 10/1993 | Nolan et al. |

(Continued)

FOREIGN PATENT DOCUMENTS

| EP | 1 197 907 A2 | 4/2002 |
| JP | 2000123098 A | 4/2000 |

(Continued)

OTHER PUBLICATIONS

American Health Consultants, Inc., "Second of 2 parts Military telemedicine developments are a test for future applications", Feb. 1, 1997, The BBI Newsletter, vol. 20, No. 2.

Business Word, Inc., "Ambulance crews use Palm handhelds to collect patient data at emergency scenes", Jan. 2002, Health Care Strategic Management, vol. 20, No. 1, p. 4 (2).

Clarke, Patrick, E., "In the Palm of Your Hand", Military Medical Technology, Apr. 15, 2003, pp. 38-42, vol. 7, Issue 3.

(Continued)

*Primary Examiner* — Sheetal R Rangrej
(74) *Attorney, Agent, or Firm* — Elizabeth Arwine

(57) ABSTRACT

A system and method used to create a longitudinal medical record for an injured person that in at least one embodiment begins a location remote from a medical facility. The system includes in at least one embodiment a plurality of mobile computing devices. In at least one embodiment, the mobile computing devices provide an interface for receiving information from a first responder or a medic.

11 Claims, 30 Drawing Sheets

(56) References Cited

U.S. PATENT DOCUMENTS

| | | |
|---|---|---|
| 5,301,105 A | 4/1994 | Cummings, Jr. |
| 5,301,319 A | 4/1994 | Thurman et al. |
| 5,307,263 A | 4/1994 | Brown |
| 5,325,478 A | 6/1994 | Shelton et al. |
| 5,337,405 A | 8/1994 | Lindauer et al. |
| 5,410,704 A | 4/1995 | Norden-Paul et al. |
| 5,482,050 A | 1/1996 | Smokoff et al. |
| 5,517,405 A | 5/1996 | McAndrew et al. |
| 5,546,580 A | 8/1996 | Seliger et al. |
| 5,557,514 A | 9/1996 | Seare et al. |
| 5,572,421 A | 11/1996 | Altman et al. |
| 5,583,758 A | 12/1996 | McIlroy et al. |
| 5,592,945 A | 1/1997 | Fiedler |
| 5,594,638 A | 1/1997 | Iliff |
| 5,682,526 A | 10/1997 | Smokoff et al. |
| 5,732,401 A | 3/1998 | Conway |
| 5,758,095 A | 5/1998 | Albaum et al. |
| 5,772,585 A | 6/1998 | Lavin et al. |
| 5,809,476 A | 9/1998 | Ryan |
| 5,840,586 A | 11/1998 | Davies |
| 5,845,253 A | 12/1998 | Rensimer et al. |
| 5,867,688 A | 2/1999 | Simmon et al. |
| 5,867,821 A | 2/1999 | Ballantyne et al. |
| 5,876,351 A | 3/1999 | Rohde |
| 5,899,998 A | 5/1999 | McGauley et al. |
| 5,924,074 A | 7/1999 | Evans |
| 5,933,809 A | 8/1999 | Hunt et al. |
| 5,935,078 A | 8/1999 | Feierbach |
| 5,939,277 A | 8/1999 | Rakowicz-Szulczynska |
| 5,964,700 A | 10/1999 | Tallman et al. |
| 5,970,466 A | 10/1999 | Detjen et al. |
| 5,974,389 A | 10/1999 | Clark et al. |
| 6,006,120 A | 12/1999 | Levin |
| 6,010,912 A | 1/2000 | Davies |
| 6,022,695 A | 2/2000 | Beard et al. |
| 6,033,076 A | 3/2000 | Braeuning et al. |
| 6,047,259 A * | 4/2000 | Campbell et al. ............ 705/3 |
| 6,055,506 A | 4/2000 | Frasca, Jr. |
| 6,082,776 A | 7/2000 | Feinberg |
| 6,155,603 A | 12/2000 | Fox |
| 6,206,829 B1 | 3/2001 | Iliff |
| 6,283,761 B1 | 9/2001 | Joao |
| 6,304,848 B1 | 10/2001 | Singer |
| 6,416,480 B1 * | 7/2002 | Nenov ............ 600/557 |
| 6,494,830 B1 | 12/2002 | Wessel |
| 6,496,702 B1 | 12/2002 | Lockhart |
| 6,581,038 B1 | 6/2003 | Mahran |
| 6,603,464 B1 | 8/2003 | Rabin |
| 6,684,188 B1 | 1/2004 | Mitchell et al. |
| 6,699,188 B2 | 3/2004 | Wessel |
| 6,790,178 B1 | 9/2004 | Mault et al. |
| 6,876,780 B1 | 4/2005 | Nielsen et al. |
| 6,876,972 B1 | 4/2005 | Kameda |
| 6,988,075 B1 | 1/2006 | Hacker |
| 7,286,894 B1 | 10/2007 | Grant et al. |
| 7,490,048 B2 | 2/2009 | Joao |
| 7,778,848 B1 * | 8/2010 | Reeves ............ 705/3 |
| 7,899,687 B2 | 3/2011 | Morris |
| 2001/0034631 A1 | 10/2001 | Kiselik |
| 2001/0049610 A1 | 12/2001 | Hazumi |
| 2002/0016720 A1 | 2/2002 | Poropatich et al. |
| 2002/0052843 A1 | 5/2002 | Canon |
| 2003/0069759 A1 | 4/2003 | Smith |
| 2003/0078806 A1 | 4/2003 | Kudryk et al. |
| 2004/0006553 A1 | 1/2004 | De Vries et al. |
| 2004/0015132 A1 * | 1/2004 | Brown ............ 604/131 |
| 2004/0078227 A1 | 4/2004 | Morris |
| 2005/0131738 A1 | 6/2005 | Morris |
| 2005/0182656 A1 | 8/2005 | Morey |
| 2012/0041782 A1 | 2/2012 | Morris |

FOREIGN PATENT DOCUMENTS

| | | |
|---|---|---|
| JP | 2000506291 A | 5/2000 |
| JP | 200152073 A | 2/2001 |
| JP | 2001052089 A | 2/2001 |
| JP | 2001134694 | 5/2001 |
| JP | 2002092537 A | 3/2002 |
| WO | WO9732271 A1 | 9/1997 |
| WO | WO9811820 A1 | 3/1998 |
| WO | WO0028460 A2 | 5/2000 |
| WO | WO0045301 A1 | 8/2000 |
| WO | WO0106339 A2 | 1/2001 |

OTHER PUBLICATIONS

Fackler, J.C., et al., "Integration of Intermittent Clinical Data with Continuous Data from Bedside Monitors", Sixth Annual IEEE Symposium on Computer-Based Medical Systems, Jun. 13-16, 1993, pp. 289-294.

Fleming-Michael, Karen, "Medics' Powerful Tool Tracks Care, Provides Info", Fort Detrick Standard, May 1, 2003, pp. 8-9.

Hamilton, Robert A., "Using a Computer to Diagnose Illnesses", New York Times, Jun. 13, 1993, p. CN4.

Hartman, R., et al., "Revolutionizing Point-of-Care Health Information System: Early User Evaluations of the Battlefield Medical Information System: Tactical (BMIS-T)", presentation at American Telemedicine Association Conference, Apr. 30, 2003.

Microsoft Corp., "Case Study: U.S. Military Improves Medical Care, Tactical Advantage with Wireless Point-of-Care Handheld Assistant", Microsoft Windows Mobile Customer Solution Case Study, http://www.microsoft.com/windowsmobile/, Dec. 2003, pp. 1-5.

Miller, Suzanne M., "Enhancing Adherence Following Abnormal Pap Smears Among Low-Income Minority Women: A Preventive Telephone Counseling Strategy", Journal of the National Cancer Institute, May 21, 1997, pp. 703, vol. 89, Issue 10.

Nielsen, P.E., et al., "Standard Obstetric Record Charting System: Evaluation of New Electronic Medical Record", Obstetrics & Gynecology, Dec. 2000, pp. 1003-1008, vol. 96, No. 6.

Onley, D.S., et al., "Medics Tap Patient Data", Government Computer News, Apr. 7, 2003, vol. 22, http://www.gnc.com.

Petroni, M., et al., "An Automatic Speech Recognition System for Bedside Data Entry in an Intensive Care Unit", Proceedings of the 33rd Midwest Symposium on Circuits and Systems, Aug. 12-14, 1990, pp. 791-794.

Saab, E., et al., "Data Modeling and Design of a Patient Data Management System in an Intensive Care Unit", Fifth Annual IEEE Symposium on Computer-Based Medical Systems, Jun. 14-17, 1992, pp. 54-63.

Sinha, V., "Telemedicine Gains Ground on the Battlefield", Government Computer News, Feb. 24, 2003, vol. 22, http://www.gnc.com.

U.S. Army European Regional Medical Command, "Standard Obstetrics Record Charting System: Delivering into the Future", European Regional Medical Command, probably available prior to Dec. 23, 2000, pp. 1-6.

U.S. Medicine, Tommy Joe Morris—Care Support on the Battlefield and Beyond, Aug. 2004, http://www.usmedicine.com/article.cfm?articleID=916&issueID=65.

Wilson, Janet D., et al., "Nurse Counseling for Women with Abnormal Cervical Cytology Improves Colposcopy and Cytology Follow Up Attendance Rates", Sexually Transmitted Infections, Aug. 2000, pp. 322, vol. 76, Issue 4.

Yajima, Nobuyuki, "IC Card Spreading over in Earnest in Japan, U.S.A. and Europe, Various Uses from Office Automation, Settlement and Business Support Tools", NIKKEI Computer, Dec. 7, 1987, pp. 62-69, No. 162, Nikkei McGraw-Hill.

Unknown author, "Consult Tracking", Jun. 2000, pp. 1-47.

Kritz, Francesca Lunzer, "Bye-bye, Paper Rx? E-Prescribing Could Boost Convenience, Safety-Given Time", Jul. 1, 2003, The Washington Post, pp. F1, F4.

Casberg, Melvin A., "Civil Defense Emergency Treatment of Burns in Mass Casualties," California Medicine Journal, Oct. 1955, pp. 289-294, vol. 83, No. 4.

* cited by examiner

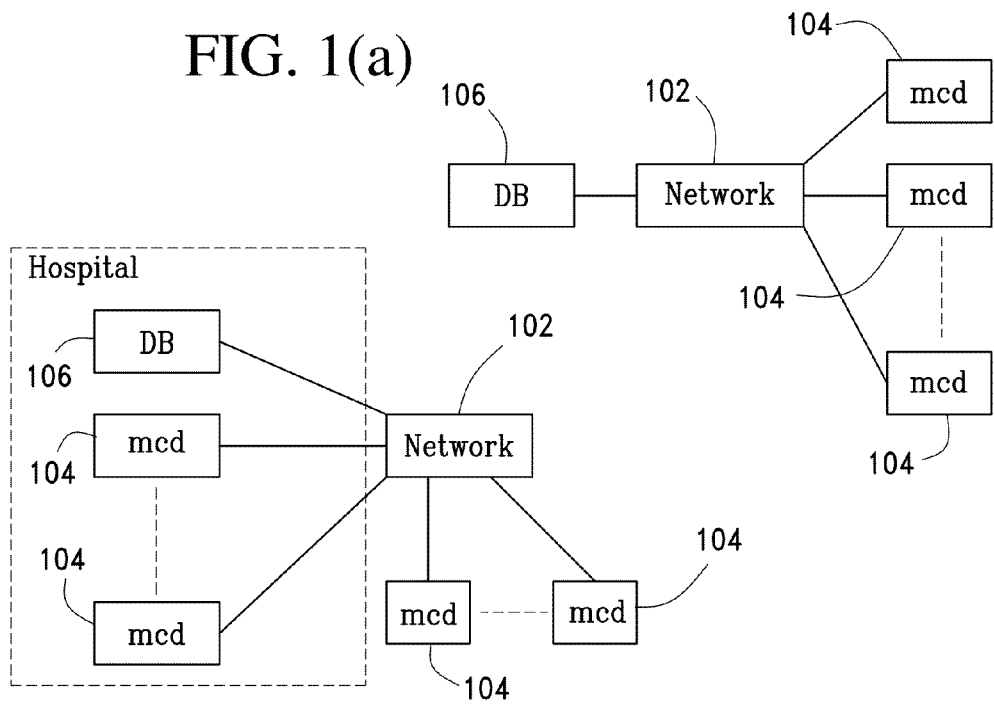
FIG. 1(a)
FIG. 1(b)
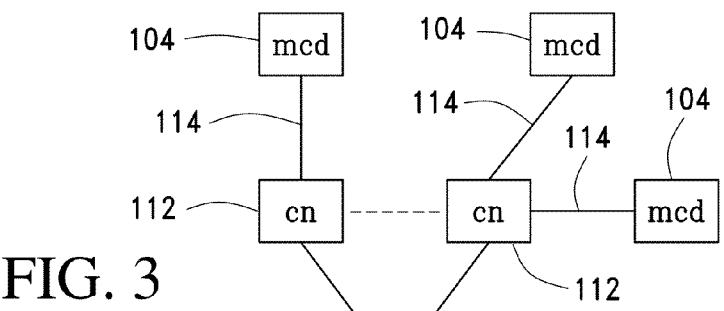
FIG. 3
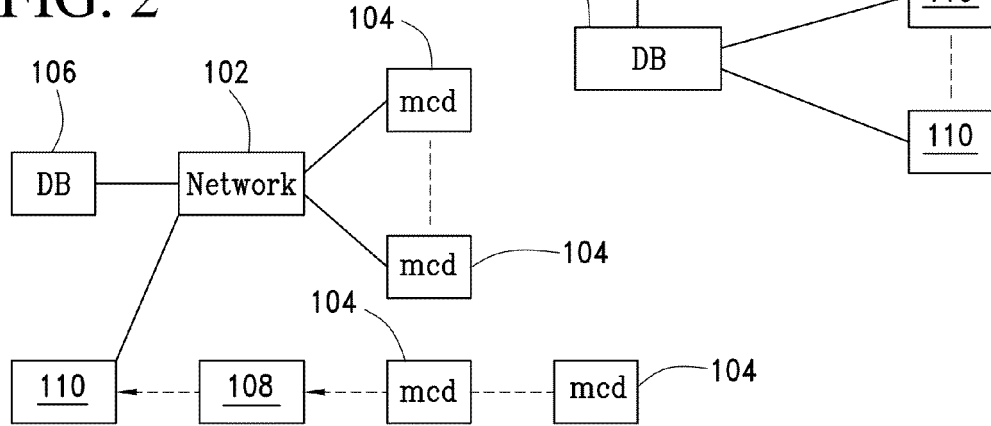
FIG. 2

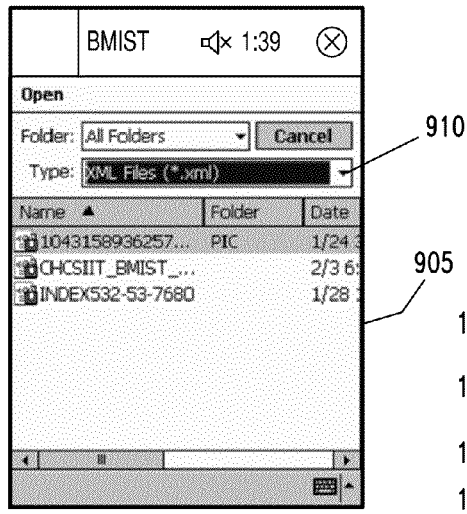
FIG. 9(b)
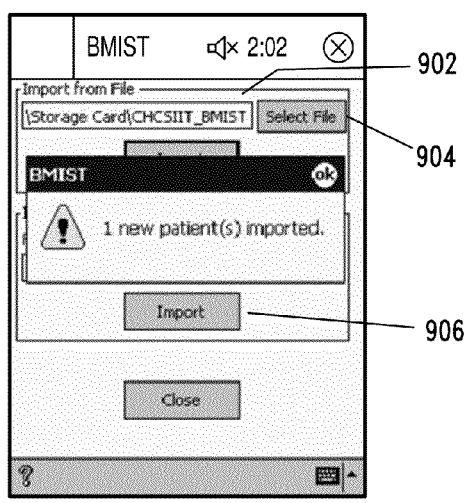
FIG. 9(c)
FIG. 10

FIG. 13

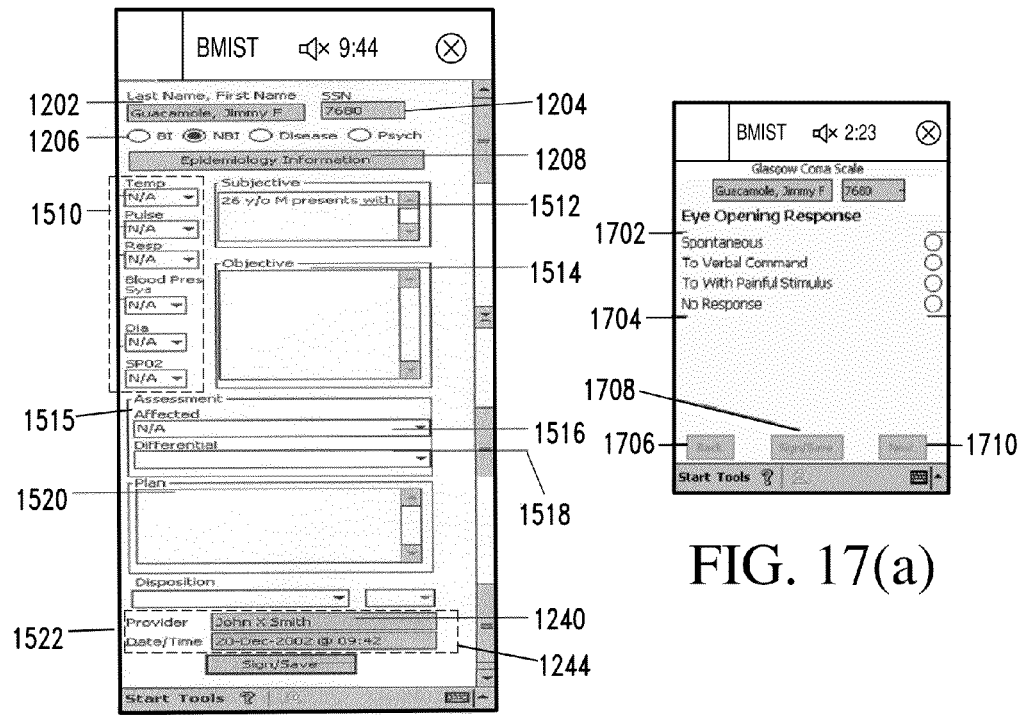
FIG. 15
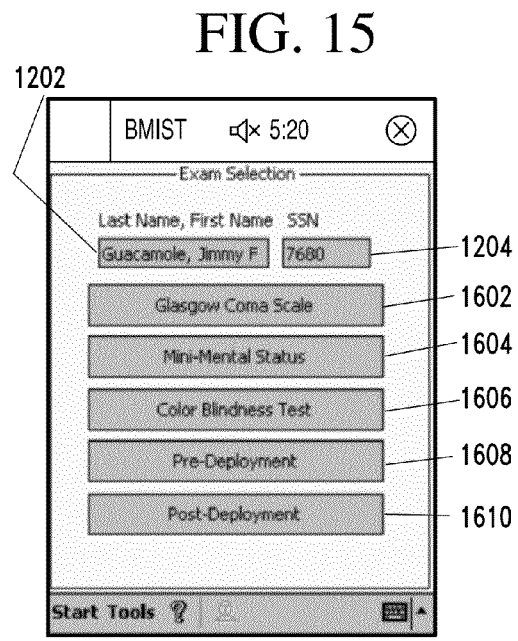
FIG. 16
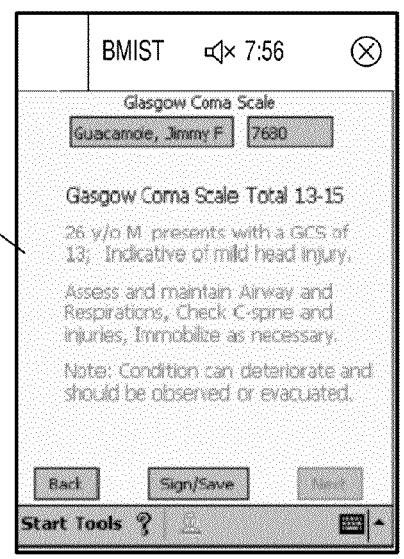
FIG. 17(a)
FIG. 17(b)

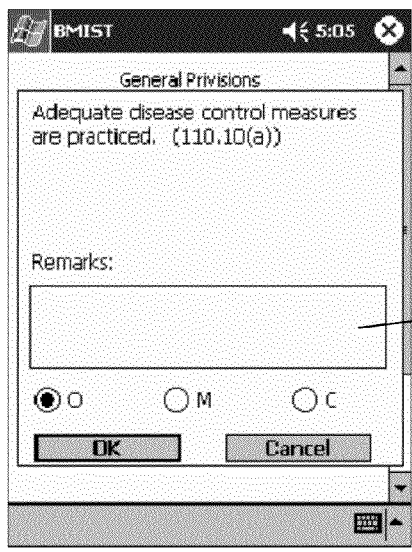
FIG. 25(g)
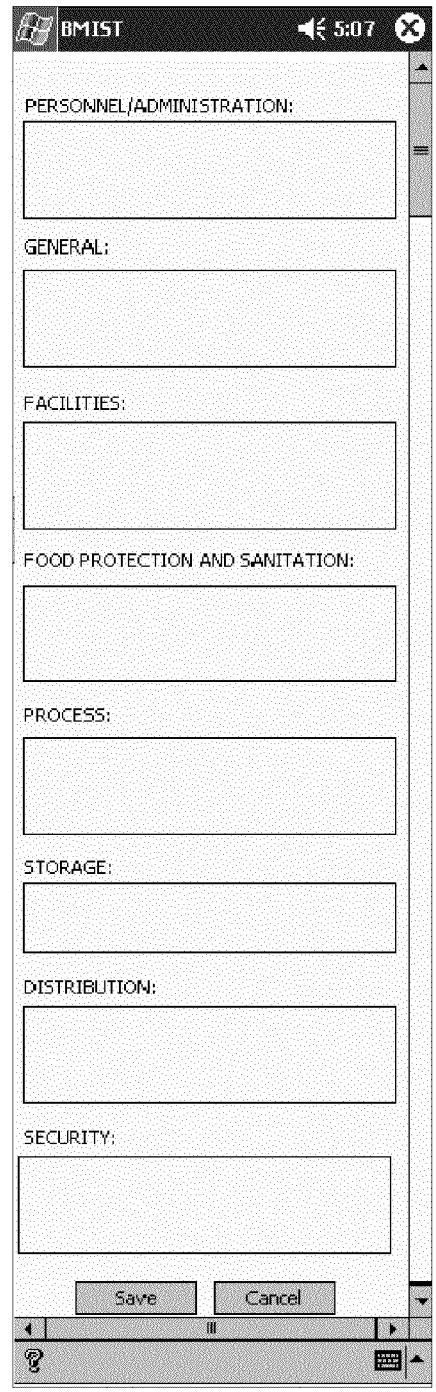
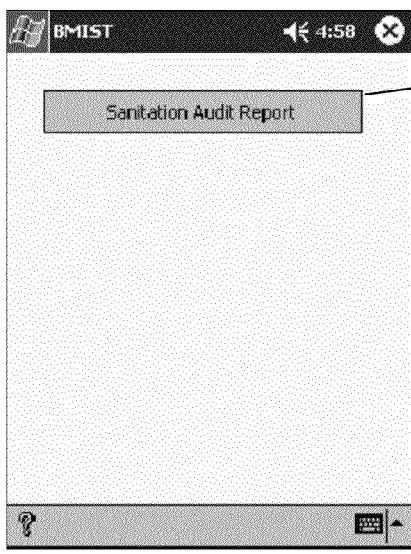
FIG. 25(i)
FIG. 25(h)

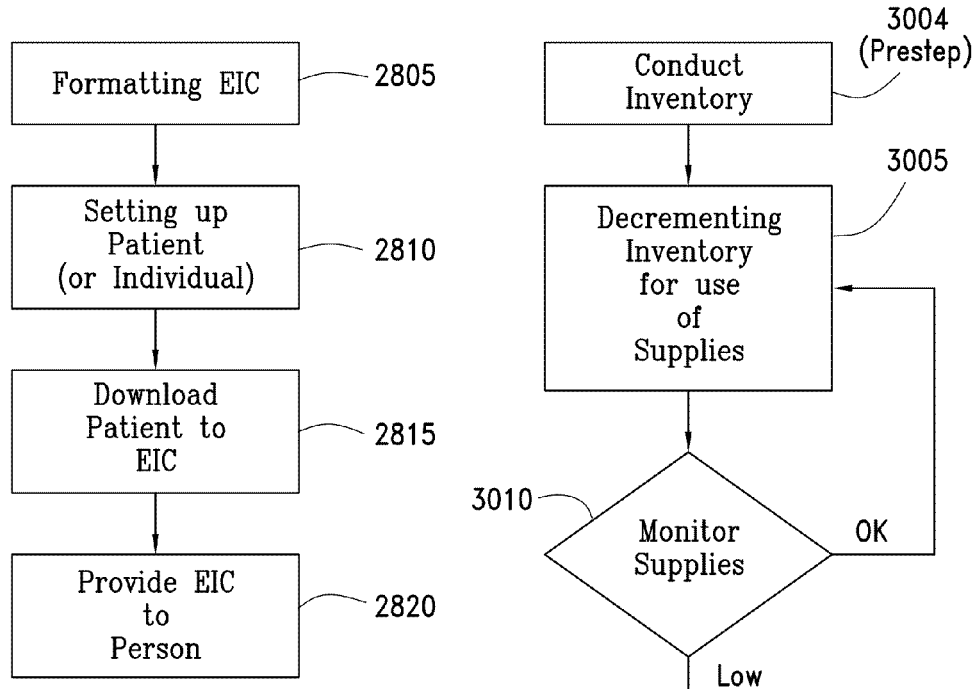
FIG. 28
FIG. 30
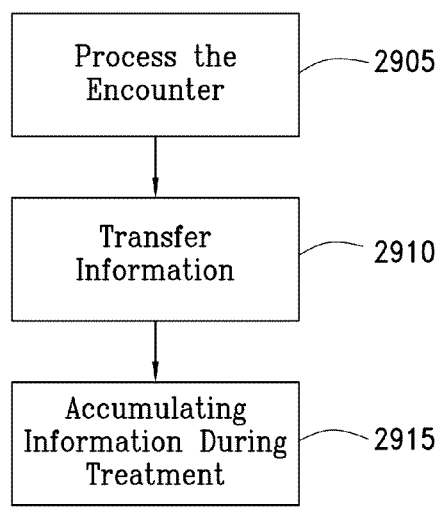
FIG. 29

MEDICAL INFORMATION HANDLING METHOD

This application is a divisional application of U.S. application Ser. No. 13/009,372, filed Jan. 19, 2011, which is a continuation application of U.S. application Ser. No. 10/438,327, filed May 15, 2003, which claims the benefit of U.S. provisional Application Ser. No. 60/381,058, filed May 15, 2002. All three applications are hereby incorporated by reference.

I. FIELD OF THE INVENTION

This invention relates to the medical records field, and more particularly, to a system for providing a longitudinal medical record.

II. BACKGROUND

There are a variety of existing medical record systems that range from pen and paper systems to electronic medical record systems. These systems have been developed for use within a particular doctor's office or other medical facility, but have not been adapted for use by first responders or far forward casualty response due to the inherent infrastructure requirements and primary focus of those systems, which generally has been recording of doctor's notes and/or ordering prescriptions.

The U.S. Army Medical Research and Materiel Command (USAMRMC) Telemedicine & Advanced Technology Research Center (TATRC) at Fort Detrick, Md., has been and is continuing to investigate utilization of commercially available, "off-the-shelf" (COTS) hand-held wireless devices for use in routine medical care in military environments. The objective has been and continues to be to improve military health care by improving medical decision making and reducing errors beginning at the point of care. Application of wireless information technologies to medical informatics and telemedicine applications at the point of care can achieve these objectives by 1) improving accuracy and efficiency of point of care data entry, thereby improving the quality of the medical records used in medical decision making and 2) providing immediate access at the point of care to key information and knowledge needed by military health care providers to make informed medical decisions. A system that satisfies these objectives is further needed to facilitate improved point-of-care diagnostic, epidemiology collection and bioinformatics tool. Specific areas identified to improve and satisfy these objectives are medical readiness, medical assessments and treatment, medical reporting and documentation, medical skills training, medical supply, and security of medical information. In each area information was gathered through research, practical experience, interviews, and literature searches.

Medical readiness was analyzed by conducting a review of the processing of 22,000 soldiers through a readiness site. The U.S. Military medically processes soldiers prior to every deployment whether training or real world in order to maintain a high state of medical readiness. The process is referred to as a Preparation for Oversees Movement (POM) or as the Soldiers Readiness Program (SRP). This process is accomplished by manually screening the outpatient health records, verification of required information and filling in a form on every individual to establish a field medical record.

This process currently requires many man hours of preparation and the medical part of the POM process currently takes an average of 6-8 hours using 4-6 medical screeners to medically process a Battalion sized element of approximately 500 personnel. (The times do not include the return visits for Physical completion). During the POM process individual medical deficiencies are identified such as missing immunizations, allergy alert tags when required, outdated physicals, glasses, inserts if required and any current medications. In addition to any health related issues and physical limitations that could render the soldiers non-deployable. Once identified efforts are made to correct these deficiencies during the screening process. During the time of this study both active military and reserve military components where processed.

The units observed were at varying levels of medical readiness and deficiencies could have easily been identified if the readiness information was in computerized format. The soldiers who were deployable could accurately and efficiently be identified as not requiring processing through the readiness site. This would greatly reduce the time it takes to medically process personnel from 6-8 hours easily to 3-4 hours. In addition if this information was made available electronically it would allow commanders immediate access to readiness information that would be previously unobtainable without going through the screening process.

An analysis of the medical assessment and treatment process was performed. In combat arms units and troop medical clinics there are three environments for medical assessment and treatment that are identifiable for combat medics and first responders in the U.S. Army. The first environment is the home station where the soldiers are in a garrison environment at their unit of assignment and the medical screening process takes place by combat medics either in the company area, the battalion aid station, or the troop medical clinic. At the home station, medics have access to the Soldiers Outpatient Medical Records and authorized sick call medications and supplies to be used within their scope that they normally do not have the capacity to carry with them while they are in field environments. The Medics are responsible for primary triage and treatment of soldiers for sick call using the HSC PAM 40-7-21 Ambulatory Patient Care, Algorithm Directed Troop Medical Care or by practical knowledge obtained while working in a health clinic with physicians assistants or physicians. The patient encounter and collection of information begins with the medical screeners and continues throughout the patients screening process. Once screened the soldiers are either given medications, treatments or sent to the physician or physicians assistant for further evaluation and treatment. If the patients received treatment by a medic, a physician or physicians assistant will verify the treatment and sign off on the encounter.

The next environment is the training environment, which is when units or elements of the unit are deployed either to a local field training environment or tactical training environments. The medics are responsible for primary triage and treatment of soldiers for battle injuries, non-battle injuries, disease, psychological and sick call. The combat medics that were interviewed and assigned to the combat arms unit that served as the base of this study received minimal training in these areas and were generally not well trained due to the unit's requirement for the medics to maintain a high level of readiness of their assigned vehicles thus decreasing the amount of training required for medics to maintain a high level of medical proficiencies.

In the study group, there were eight medics with two assigned to each company, one of the medics per pair of companies was a senior medic and the other three were combat medics. In all but two instances the medics were left to their own devices when it came to the initial triage and treatments of soldiers in the training environments. In the other two instances the soldiers were evacuated immediately without the required field medical cards. In the rest of the cases reviewed soldiers received inadequate medical treatment and were returned to duty until the unit or element returned to home station ranging from 24 hours up to 30 days. Upon return to home station, soldiers were then re-screened then treated as appropriate. In addition in all 40 of the cases that were screened for sick call in the field environment none of the required information was collected at the initial point of care nor were the medical supplies (Class VIII) accounted for in these treatments. During each of the training exercises soldiers were each issued MILES casualty cards and when the soldier becomes injured through the training simulation he reads the MILES cards and presents the medic with the symptoms listed on the cards. The medics are then responsible for the triage and treatment of the soldiers as necessary and as appropriate. This encounter is then documented on a Department of Defense 1380 Field Medical Card. Approximately 820 personnel from each company became casualties depending on the scenarios. By the time the casualties reached the Level I Battalion Aid station approximately 50% of the casualties had varying levels of treatment and approximately 10% had the required DD form 1380 and 50% of those had the required information filled in on the Field Medical Card. At the battalion aid station the medics and providers initiated the missing field medical cards and filled in the missing treatments but in most cases lacked the necessary information to complete the initial encounter information due to lack of knowledge of the circumstances surrounding the injuries.

The last environment studied was the deployed state, which is when units are deployed to an operational environment either in the United States or in foreign countries. This part of the study was conducted using practical experience and interviews and review of medical information. In this environment, the medics are responsible for primary triage and treatment of soldiers for battle injuries, non-battle injuries, disease, psychological and sick call. The medics have limited resources and are generally left to their own devices to maintain unit medical readiness and treatment during operations other than war such as humanitarian missions and peace keeping operations. They are also required to conduct triage and treatment of soldiers during high intensity conflicts and acts of war. During these deployments medics were provided little to no communications at all. Of the three cases reviewed: one soldier received combat related injuries, one solider was evacuated due to stress related issues, and the third soldier had a dermatological condition that was treated and returned to duty. Of the three cases the soldier that had combat related injuries received lifesaving treatment and was evacuated, the encounter was documented on a small piece of paper which upon review of the health record showed that is was lost and the soldier had to be re-screened and the treatments had to be estimated. In case number two, the soldier was evacuated and the required encounter was not documented prior to evacuation. In the third case, the soldier was treated and returned to duty and the required information was not documented and a follow-up was scheduled and the initial treatment was re-initiated and documented at that time.

The required training to maintain medical skills proficiency is either not being conducted or is inadequate to provide the required skill sets for the combat medics. The initial training provided to combat medics is insufficient to prepare them to conduct sick call at the unit level and in field environments. The required information is not being adequately collected or documented at the point of care and point of injury possibly due to insufficient emphasis being put on the requirement or due to the time it takes to document an encounter. Forty medics were provided various combat injury scenarios and had them fill in the required elements on a field medical card. It took the 40 medics an average of 3-5 minutes to fill in the initial encounter. This could have a negative impact on the required lifesaving treatment of combat injuries especially during a mass casualty scenario. The lack of documentation of the treatment at the initial point of treatment could also cause unnecessary administration of additional medications thus causing clinical errors after initial triage. Providers would be more likely to capture this information at the point of care/point of injury if there could be an impact on the time it takes to document the encounter on the field medical card. During both the training and deployed environments, medics had little to no communications available to them to request resupply and had to rely on a supply request written on notepads and in some case did not get re-supplied until returning to their respective home station. If medics were provided organic communications they could have immediate access to more experienced providers and could then provide better medical care in the deployed environment well as provide immediate information for medical reporting which is important for not only clinical treatment, command and control but also resupply of class VIII medical supplies.

An analysis of medical reporting and documentation was conducted through practical experience, review of outpatient health records, interviews and review of literature. On average, 25,000 pages of documents and forms pour into the DoD Medical Records every day. Requests for service, such as sick call, are a daily occurrence; efforts to provide that service promptly were once a struggle. Medical reporting is currently accomplished by collecting log sheets and collating them from the referring units and questionnaires completed by both referring and consulting doctors. See "Presidential Advisory Committee on Gulf War Veterans' Illness Final Report, 1996".

A review of a set of 5000 outpatient health records for active duty soldiers provided a set of 492 records that were for combat related injuries. Of those 492 records there was just one Department of Defense Form 1380 Field Medical Card present, which indicates that information was getting lost or not captured at all and in accordance with AR (Army Regulation) 40-66, Medical Record and Quality Assurance Administration that requires the DD form 1380 and all health care information collected is required to be maintained in the health care records. The Medical Records Section and the Personnel Administration Division Officer responsible for these records indicated that the DD form 1380 is not required to be maintained in the outpatient health record and that it is usually destroyed.

Due to insufficient training of medical records personnel and/or lack of information collected at the point of care/point of injury medical information is lost, not captured or destroyed. If there were a means by which to capture this information in a computerized format there would be 1) an increase in the efficacy of the information, 2) tracking capability for epidemiological information, and 3) immediate access to medical information for command and control based on the computerized clinical encounters.

The next part of the analysis was conducted by practical experience, observation and interviews related to the skills training of the medics. In combat maneuver battalions, the qualifications of the combat medics vary depending on educational background, experience and motivation. Medics are provided initial training for responding to combat related injuries and rudimentary clinical documentation. It is generally left up to the unit of assignment to provide further skills training for soldiers. As the soldiers go up in rank they are sent to more advanced medical training or Special Forces medical training. The more skilled medics, physicians and physicians assistant are responsible to train the lesser skilled medics during scheduled training times and through practical experience. Of the combat medics observed and interviewed, they typically lacked the sufficient skills to respond to real world injuries and sick call screening, unless they had been assigned to a Medical Center or health clinic during their early career. There were extreme skills deficiencies of the medics that were directly assigned to combat arms units from their initial training.

The focus for training in the combat arms units were on vehicle maintenance and it was expected that medics were highly trained prior to being assigned to the unit. In addition medics received training one day per week on medical skills and/or training on how to pass the Expert Field Medical Badge training. This training was complimentary to training medics to a high level of proficiency in field medicine for combat injuries, but this training lacked severely in training medics on how to provide treatment for sick call or non-combat related injuries. One way to address this would be to have a skills trainer or training device that could help to facilitate interactive training for combat medics and Special Forces medics.

The next part of the analysis was accomplished through practical experience, observation and literature research and related to medical supply. When in a training or deployed environment, Class VIII medical supplies are generally ordered after a manual inventory of supplies is conducted, then the supplies are ordered when communications become available or through sending supply request on notepads. Of all of the medics interviewed they were not documenting the medical supplies that were used for training, deployments or for sick call in field environments. At the battalion aid station supplies were inventoried and reordered monthly or as needed for sick call. The medical supplies in the combat load were inventoried either annually or during a major deployment as necessary.

During both the training and deployed environments, medics had little to no communications available to them to request resupply and had to rely on supply requests written on notepads and in some case did not get re-supplied until returning to their home station. This form of resupply leads to a decrease in the combat readiness of the medics limiting their ability to continue to provide medical treatment to the soldiers at the initial point-of-care.

This last part of the analysis was accomplished through practical experience and observation and related to the security of the medical information. The security of medical information for the combat medic is limited to the physical security of health care information by the combat medic.

Most combat medics carry a leader's book which contains some soldier information, medical information such as current medications, allergies and possibly some medical history. Medics also are required to capture information on Field Medical Cards DD 1380, when they capture the information they remove an onion skin (protective Paper) and maintain a copy of each encounter in the Field Medical Card Book. Each encounter not only contains medical information but also the soldier's demographics and unit information. At the battalion aid station, they maintain the outpatient health records in filing cabinets that are maintained by medics and assigned personnel.

The security of medical information at the point of care at the level of the combat medic is inadequate to today's emerging health care security standards and could provide potentially vital tactical information to hostile forces if lost or if the medic is captured. The current field medical cards and accompanying book that maintains the copies of the field medical cards can not easily be torn up, nor can they be easily burned or destroyed. If the information is in computerized format on a handheld device the information could be made more secure and even easily erased to preclude the information getting into the hands of anyone but the intended provider.

On the backdrop of the above analysis, there is a Presidential Review Directive 5 that mandates development of a standardized, integrated and seamless system of medical command and control for the military medical community within Global Command and Control System (GCCS) to include an individually carried device.

The Department of Defense is currently funding the Composite Health Care System II (CHCS II) program intended to produce a clinical information and medical information management support system for military peacetime health care facilities as a follow-on to the current CHCS (I) system which currently provides medical administrative information management, ancillary services support and order entry for both inpatient and outpatient care in most fixed DOD health care facilities. While CHCS II is intended as a point of care system to support most health care provider information processing needs, it is limited by placement of desktop PCs or location of laptop PC LAN "plug-in" locations. To the best of the present inventor's knowledge, a truly portable, pocket-sized PC tool is not being provided by the CHCS II system.

DOD (HA) has also designated a program manager for deployable military health care information processing systems development. The Theater Medical Information Program (TMIP) is charged with identifying requirements and developing deployable medical information systems for the DOD. As yet the TMIP has not fielded a point of encounter clinical information system for deployable medical units. A PC based version of CHCS I has been used within some deployable military hospitals on an experimental basis. Each service is also charged with producing service-specific TMIP applications for far-forward applications within service specific areas of support and for adapting its deployable computer hardware or acquiring service supportable hardware to support both service specific and joint TMIP applications.

The Air Force TMIP application is called "Care in the Air". This program is currently testing PSC-5 UHF SATCOM radios to support medical data transmission from Air Force aircraft; this UHF radio system already exists on Air Force aircraft for support of Army ground missions. Air Force medics, testing demand access to aircraft data, must be able to access data "seamlessly" from a "netcentric" database and be able to pull out demographic data, identify the location and point of injury, and initial treatment provided. Even though this mission is one of that requires significant individual provider mobility, the Air Force is still using laptop PCs and bubble jet printers in conjunction with backpack ground terminal radios. No handheld PC point of care system is currently included in the Care in the Air program even though such a system would help solve mobility issues stemming from the cumbersome nature of the systems currently being tested.

The Army deployable medical information systems program is called Military Communications for Combat Care (MC4). MC4 is primarily concerned with acquiring the hardware and communications systems to support Army medical command and control and the DOD TMIP program. However, MC4, has identified the need for a handheld notebook computer or personal data assistant for first responder Army medics. To test that concept the MC4 has spent significant resources developing an inflexible Windows CE medical encounter data recording application that is so proprietary and so rigid in its design that it cannot be readily expanded or adapted for use by military health care providers beyond first responder medics without significant redesign and software reengineering. What is really needed at this level is a system that can be configured or tailored by users at each level of the military health care continuum to meet situation specific information processing needs without retraining.

The Navy version of the Theater Medical Information Program, TMIP Maritime, is also pursuing a parallel path toward a deployable medical informatics support system. The Navy has worked on deployable computerized medical monitoring and patient registration systems, "wireless" data gathering from a Navy version of the "Personal Information Carrier" medical data tag, and various medical image acquisition and transmission systems. None of these projects have produced a versatile handheld personal data assistant capable of meeting all of the point of encounter medical information needs of providers at multiple levels of the military health care system.

The U.S. Army Medical Department Center and School (AMEDD C&S) has developed an approved Tables of Organization and Equipment (TOE) for Medical Reengineering Initiative (MRI) Combat Support Hospitals and for the Medical Detachment (Telemedicine), a specialized unit intended to provide immediate short term medical command and control communications and telemedicine support for an Army TOE Medical Brigade. These TOES include requirements for organic broadband multi-mode (voice, data, video) telecommunications switches for each MRI TOE Combat Support Hospital and satellite earth stations for each of the 6 deployable teams which make up a Medical Detachment (Telemedicine). These teams are intended to bridge the gap between the dynamic modern communications needed for highly deployable, state of the art military health support and the military bandwidth relegated to and outdated communications systems available to deployable U.S. military health care organizations. While these teams are intended to provide some highly mobile telemedicine and medical informatics capabilities to rapidly deploying medical units, the teams will not be equipped with the type or numbers of personal handheld systems required by first responders and forward deployed physicians for point of encounter medical information processing support.

The U.S. Army Medical Research and Materiel Command and the AMEDD C&S have collaborated since 1996 with the Signal Battle Command Battle Lab Gordon (BCBLG) to integrate telemedicine and satellite communications capabilities into the Army Warfighter Information Network-Proof of Concept (WIN-POC) mobile communications switch, as a platform for providing multi-user broadband medical command and control communications and telemedicine connectivity. This capability was successfully demonstrated in 1999 at the Joint Readiness Training Center (JRTC), Fort Polk. The medical WIN-POC is intended to provide sustained broadband communications from forward deployed areas and joint task force headquarters locations rearward to the Theater and National Military Command Headquarters and Military Health System Medical Centers worldwide. The WIN-POC has a deployable state-of-the-art Asynchronous Transfer Mode communications switch that is capable of receiving and transmitting voice, data and video simultaneously from multiple deployed sites using either military or commercial radio, wired, wireless or satellite communications. The WIN-POC can also be equipped with a local cellular or other wireless telephone switch to provide both local and long distance telephone service. Satellite connectivity through the WIN-POC using a Very Small Aperture Terminal (VSAT) satellite earth station was also demonstrated at the JRTC. This capability is intended for deployed medical facilities through area or direct support common user communications facilities that are part of the Army Warfighter Information Network-Terrestrial (WIN-T) concept.

The Joint Medical Operations-Telemedicine (JMO-T) Advanced Technology Demonstration (ACTD) conducted by the U.S. Pacific Command during the period FY1999-FY2002. The operational concepts of this ACTD were embodied in five interrelated pillars: Forward Health Care, Information Superiority, Net-Centric Communications, Theater Telemedicine Force Package, and Medical Mission Planning and Rehearsal. The ACTD explored the conceptual feasibility of leveraging emerging information technologies to support those operational concepts. The JMO-T ACTD attempted to provide satisfaction of critical Warfighter operational issues with the insertion of mature medical, telecommunications, and information technologies. Demonstration and evaluation used planned joint exercises as platforms to employ the target capabilities, collect and analyze performance data, and derive user acceptance conclusions. Technologies employed to achieve these advanced concepts included handheld data input devices, digitized medical equipment sets, mobile communication devices, and wireless technologies. The centerpiece of the ACTD was the deployable theater telemedicine force package, designed to provide early-in hardware, software, and communication capabilities for the collection and sharing of critical medical information from far forward on the battlefield. Digital medical imaging equipment; interoperable telemedicine teams; and computerized, interactive medical force planning and rehearsal tools are being leveraged to provide enhanced force medical protection under Joint Vision 2010 operational concepts. While the JMO-T ACID is leveraging many of the evolving DOD medical informatics and telemedicine tools described above, the demonstration manager has not yet identified a multi-application handheld tool for providing on-line two-way medical information support for first responders. A wireless, flexible and scalable personal data assistant that can be used by military health care providers at all levels of care from the foxhole to the medical center is the ideal tool to meet the JMO-T ACTD objective of providing useful medical informatics and telemedicine support for first responders across the spectrum of the military health care operations and continuum of support levels of care.

The Global Grid Telemedicine System (GGTS) concept which envisions leveraging emerging worldwide military and civilian communications and information processing networks to enable intelligent medical consultation routing and medical information processing is being considered as the "infosphere" architecture and communications "backbone" infrastructure on which to test the ACTD objectives described above. The U.S. Army Medical Research and Materiel Command and the U.S. Army 1108th Signal Brigade in conjunction with the JMO-T ACTD Demonstration Manager have developed a transition strategy for GGTS netcentric medical communications within the emerging Command Control Communications Computers Intelligence Surveillance and Reconnaissance (C4ISR) infrastructures. The strategy involves two research phases and an acquisition phase. Formulation of this strategy focused on identifying Government and Commercial off-the-shelf (GOTS and COTS) applications, that when combined with custom software while allowing for development consistent with the Defense Information Infrastructure Common Operating Environment (DII COE), can support the affordable development of GGTS. The JMO-T ACTD implementation of the GGTS offers an excellent opportunity to test the concept of a wireless medical enterprise in a way that insures extensive definition of the GGTS functions in collaboration with operational users.

Following the experiences with Agent Orange exposure during the Vietnam War and more recently from adverse health claims by some members deployed during the Persian Gulf War, health surveillance is becoming an essential occupational health tool for diversely deployed military troops facing myriad and often unknown environmental exposures and hazards. In response to the public outcry, Public Law 105-85 was instituted on Nov. 18, 1998, mandating the DoD to develop a deployment health surveillance system to detect and prevent health problems arising as a result of exposures during deployments and operations. Given the far-reaching concerns, associated fiscal costs, and perceptions of "cover-up" surrounding post-conflict illnesses among Gulf War veterans, it is not surprising that Congress provided legislative direction regarding military health surveillance and record keeping.

What is needed is proof of concept integration and application of commercial off-the-shelf (COTS) medical informatics, telemedicine, and wireless information technologies to (1) explore use of wireless networking in medical settings within deployable combat medics in the field, (2) test prototype systems that make use of Personal Digital Assistants (PDA) as point-of-care diagnostics, data collection, medical order entry, and knowledge acquisition tools in a wireless "net-centric" distributed computing environment, (3) web browser applications and the Internet to enable immediate access to distributed expertise and knowledge from diverse data and knowledge bases and expert medical consultants world-wide and 4) apply advanced technologies for data gathering and bi-directional transfer of vital information between the battlefield, theater operations, and home based fixed medical facilities. Models created will potentially enable an efficient and non-intrusive "behind the scenes" aggregation of data to be used for wide variety of purposes including, but not limited to, case-based medical equipment re-supply, staffing needs assessment, outcomes-based appraisals, and sundry patient/provider pattern analyses so critical in an era of managed care.

III. SUMMARY OF THE INVENTION

The invention preferably includes a wireless handheld assistant designed to record the essential elements of a medical history and physical examination and then provide the medical analysis and decision support for first responders. It uses a wireless, flexible and scalable personal data assistant that can be used by military health care providers at all levels of care from the foxhole to the medical center. It is the ideal tool to meet the military objective of providing useful medical informatics and telemedicine support for first responders across the spectrum of the military health care operations and continuum of support levels of care. The invention in at least one embodiment provides interoperability for health care providers; and computerized, interactive medical force planning and rehearsal tools are leveraged to provide enhanced force medical protection under the objective force operational concepts.

According to one embodiment of the invention, the invention is a medical information system comprising: at least one database containing medical records of a plurality of individuals, a computer network connected to said database, a plurality of mobile computing devices in communication with said computer network, each of said devices having means for maintaining a list of patients, means for receiving information from a user regarding at least one of one of the patients and a newly entered patient, the information relating to the health of the patient, means for automatically completing a portion of the information required to complete the information. The invention according to that embodiment includes having each of said mobile computing devices includes means for communicating with an EIC. The invention according to this embodiment further comprising a plurality of connection nodes in communication with said computer network, and each of said connection nodes is in communication with at least one mobile computing device. The invention according to this embodiment further defines the means for automatically completing a portion of the information supplies a narrative for injuries entered by the user using location and injury type and correlates the narrative to ICD9 codes.

According to another embodiment of the invention, the invention is a method for creating a longitudinal medical record as a digital record comprising: entering information regarding a health event of a patient into a mobile computing device at a location remote from a medical facility, transferring the information regarding the health event and the patient to the medical facility in an digital format, and accumulating additional information regarding the patient during a period of treatment at the medical center. The entering step according to one embodiment includes receiving a selection of the patient from a list of individuals, displaying an interface for receiving information about the health event, receiving the information about the health event, providing a narrative based on the information about the health event, recommending a course of treatment, and compiling the digital record for the health event.

According to one embodiment, the invention includes a method for receiving information regarding an injury received by a patient by an user comprising: displaying an interface having a series of inquiries relating to a generic injury including a type of the injury, a classification of the injury, a graphical representation of the human body, a medication section, and a vital signs section; receiving from the user identification of the type of injury and classification of the injury, receiving a location of the injury based on the user tapping at least one body part, receiving additional information regarding the injury selected from a list that is based on the injury classification, providing an injury summary based on the received information, estimating a level of consciousness of the patient based on the received information, receiving confirmation of the level of consciousness from the user, receiving information regarding medications given, receiving vital sign information, recommending a course of treatment based on the information received from the user, and requesting information about the disposition of the patient.

According to another embodiment, the invention includes a method for collecting medical information and facilitating record keeping of the medical information for a work force, the method comprising: preparing multiple personal identification cards to include medical and demographic information about one individual in the workforce, assigning the individual whose information is contained on the personal identification card their respective personal identification card, preparing multiple mobile computing devices for use by medical staff members of the workforce to have software for receiving additional health information about workforce members, instructing the medical staff members on how to use the mobile computing devices and how to exchange data between the personal identification cards and the mobile computing devices, when treating an injured workforce member, connecting the injured workforce member's personal identification card to the mobile computing device, creating a field medical record regarding the injury, continuing to monitor the patient until disposition has occurred, transferring the field medical record to the personal identification card, when the injure workforce member is sent to a medical facility, loading the field medical record from the personal identification card to a database at the medical center to create a longitudinal medical record.

The immediate short-term reach back long-haul communications afforded to medical treatment facilities deployed on short notice by the Medical Brigade's Medical Detachment (Telemedicine) and the longer term support afforded by the WIN-POC, coupled with a wireless point of care personal data assistant capability of this invention, offer unlimited opportunities for significantly reducing medical errors and improving the quality of care provided to forward deployed military personnel. Integration and deployment of these systems can provide first responders and forward deployed physician's access to critical information, knowledge, and medical consultation and can greatly improve the quality of medical data acquisition, processing and storage even at far forward points of care.

The overall aim of the invention is to provide a point-of-care wireless hand held device and support architecture to improve military health care by improving medical decision making and reducing errors. This will be accomplished through the application of wireless information technologies to medical informatics and telemedicine applications at the point of care and rearward. At least one embodiment of the invention provides a point-of-care software and architecture to be fully automated, so that an unskilled person can learn to operate the system after only brief training. The invention is being widely adopted and used in the military and governmental market as an economical means for providing immediate access to key point of care information, knowledgebases, and documentation, in telemedicine applications, where relatively unskilled health care providers can generate, transmit and receive this information real-time (when communication are available) and near real-time (when communications become available) thus empowering health care providers to make informed medical decisions.

An objective of the invention is to improve military health care by improving medical decision making and reducing errors beginning at the point-of-care. Application of wireless information technologies to medical informatics and telemedicine applications at the point-of-care can achieve these objectives by 1) improving accuracy and efficiency of point-of-care data entry, thereby improving the quality of the medical records used in medical decision making and 2) providing immediate access at the point of care to key information and knowledge needed by military health care providers to make informed medical decisions.

An advantage of at least one embodiment of the invention is the automatic ICD 9 coding of health concerns and/or injuries by the system based upon selections made by and data entered by the user (or pulled/received from a data source) in the background for later use. A further related advantage provided by at least one embodiment according to the invention is the intelligent completion of the treatment field based upon the entered information regarding the health concern and/or injury including the recommendation of drugs to administer the patient.

Another advantage of the invention is the ease of use of the invention. At least one study showed the completion of an encounter form DD 1380 to be 15 seconds to 1 minute which is down from 3 to 5 minutes using paper and 5 to 10 minutes using previous attempts to make the form electronic. With data currently collected from trials, the ease of use has led to document retention of about 82% for initial encounters which is up from a retention rate of about 8% for the paper forms. This advantage in part leads to improved data accuracy and completeness of information relating to the injury and/or health concern including, in at least one embodiment, epidemiology information. The completeness of data allows for improved analysis, for example, of a mass health event. Another facet of data completeness is creation and maintaining of longitudinal medical records from the point of health concern/injury back through post-treatment for the health concern/injury.

Another advantage obtained by at least one embodiment of the invention is scalability both in terms of the number of mobile computing units to the number and types of ways to input data into the system and have it attached to a medical record of an individual. A still further advantage of at least one embodiment is the ability to be transferred between different platforms with minimal effort.

Another advantage obtained by at least one embodiment of the invention is providing commanders with real time information about their units' readiness status and providing support for medical command and control, telemedicine and medical informatics applications across the continuum of the entire spectrum of military medical operations but especially for the first responder and far forward medical facilities.

Another advantage obtained by at least one embodiment of the invention is the ability to transmit medical data to servers in a net-centric environment providing data for readiness, medical history, consultation, evacuation and other medical planning and force health surveillance. Furthermore, the invention can serve as a tool for knowledge retrieval from multiple sources via the network it is in communication with and thus the Internet.

An advantage of at least one embodiment of the invention is the ability for individual mobile computing devices to be rapidly deployed and/or redeployed with little downtime. Preferably, this advantage is obtained by the invention being easily configured and more preferably pre-configured for the environment in which it will be used and is capable of communicating by any network and/or communication link that is able to handle IP traffic. This in itself provides an advantage of being deployable to areas that are not hardwired for a network, but instead the area is networked wirelessly.

An advantage of at least one embodiment of the invention is increased situational awareness anytime, anywhere at multiple levels of the interconnected system including the capability of real-time or near real-time command and control information.

Another advantage of at least one embodiment of the invention is the elimination of errors through error preclusion and the inability to select or enter information later on the form that would contradict the earlier entered information on that form.

A device built according to the main exemplary embodiment of the invention has been selected as the U.S. Army's choice for handheld for use as part of TMIP. TMIP has been approved for deployment with medical units to in part provide a path for information to more from forward positions back to the Joint Task Force Command level.

Given the following enabling description of the drawings, the apparatus should become evident to a person of ordinary skill in the art.

IV. BRIEF DESCRIPTION OF THE DRAWINGS

FIGS. 1(a)-3 illustrate block diagrams according to the invention.

FIGS. 4-23(e) depict different interfaces useful in an exemplary embodiment according to the invention.

Figure 4:
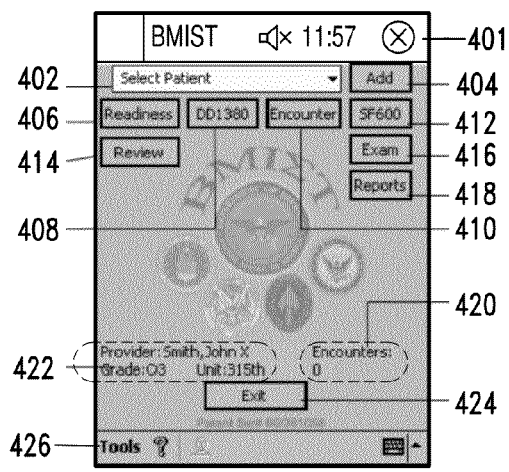

FIGS. 25(a)-(i) depict interfaces according to an exemplary embodiment according to the invention.

Figures 26A, 26B:
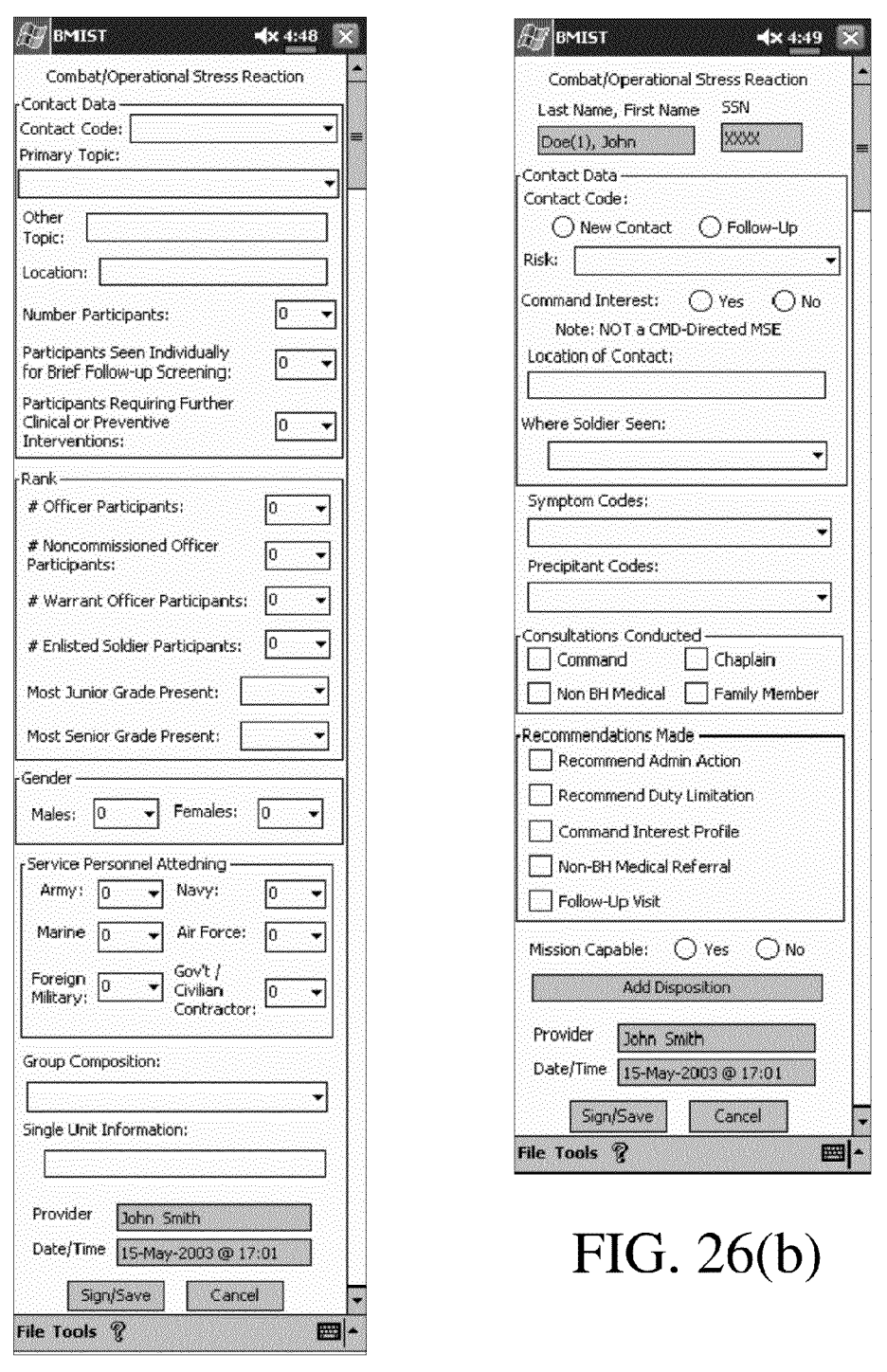

FIGS. 26(a)-(b) illustrate interfaces according to an exemplary embodiment according to the invention.

FIGS. 27(a)-(d) depict interfaces according to an exemplary embodiment according to the invention.

FIGS. 28-30 illustrate block diagrams according to exemplary embodiments according to the invention.

V. DETAILED DESCRIPTION OF THE DRAWINGS

The invention preferably includes at its highest level a medical record system including a communications network, a plurality of mobile computing devices, and at least one database. The invention at a low level preferably includes a mobile computing device such as a personal data assistant (PDA) with software (or hardwired) that allows entry of medical information in the field by a medic or other medical professional regarding a plurality of injured individuals and transmission of the medical information back to a medical facility thus creating a longitudinal medical record for the patient.

The present invention is described more fully hereinafter with reference to the accompanying drawings, in which preferred and exemplary embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. The accompanying drawings show preferred embodiments of the invention.

As will be appreciated by one of skill in the art, the present invention may be embodied as a computer implemented method, a programmed computer, a data processing system, a signal, and/or computer program. Accordingly, the present invention may take the form of an entirely hardware embodiment, an entirely software embodiment or an embodiment combining software and hardware aspects. Furthermore, the present invention may take the form of a computer program on a computer-usable storage medium having computer-usable program code embodied in the medium. Any suitable computer readable medium may be utilized including hard disks, CD-ROMs, optical storage devices, or other storage devices.

Computer program code for carrying out operations of the present invention is preferably written in a plurality of languages including ASP (Active Server Pages), HTML (Hypertext Markup Language), SQL (Structured Query Language), and C++. However, consistent with the invention, the computer program code for carrying out operations of the present invention may also be written in other conventional procedural programming languages.

The program code may execute entirely on the user's mobile computing device, as a stand-alone software package, or it may execute partly on the user's mobile computing device and partly on a remote computer. In the latter scenario, the remote computer may be connected directly to the user's mobile computing device via a LAN or a WAN (Intranet), or the connection may be made indirectly through an external computer (for example, through the Internet, a secure network, a sneaker net, or some combination).

The present invention is described below with reference to flowchart illustrations of methods, apparatus (systems) and computer programs in accordance with the several embodiments of the invention. It will be understood that each block of the flowchart illustrations and block diagrams, and combinations of blocks in the flowchart illustrations and block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means or program code that implements the function specified in the flowchart block or blocks.

The computer program instructions may also be loaded, e.g., transmitted via a carrier wave, to a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Various templates and the database(s) according to the present invention may be stored locally on a provider's stand-alone computer terminal (or mobile computing device), such as a desktop computer, laptop computer, palmtop computer, or personal digital assistant (PDA) or the like. Exemplary stand-alone computers may include, but are not limited to, Apple®, Sun Microsystems®, IBM®, or IBM®-compatible personal computers. Accordingly, the present invention may be carried out via a single computer system, such as a desktop computer or laptop computer.

According to an embodiment, the database may be centrally stored within one or more computers accessible to multiple users. Accordingly, users may access the database through a private or public computer network in a conventional manner via wired or wireless communications. By maintaining the database in a central location, updates can be easily made to the database by a system administrator without having to access all of the machines in the network.

As is known to those with skill in this art, network environments may include public networks, such as the Internet, and private networks often referred to as "Intranets" and "Extranets." The term "Internet" shall incorporate the terms "Intranet" and "Extranet" and any references to accessing the Internet shall be understood to mean accessing an Intranet and/or an Extranet, as well unless otherwise noted. The term "computer network" shall incorporate publicly accessible computer networks and private computer networks.

There are a variety of emerging commercial off the shelf wireless technologies that could be used to implement the invention. WaveLan is a wireless LAN technology that utilizes the Orinoco IEEE (PCMCIA Type II) PC Card with integrated antennas (antenna diversity)+connector for external antenna for mobile equipment (notebooks, handheld, MSD 1), with 915 MHz and 2.4 GHz versions as well as optional WEP encryption. This technology is widely used for static wireless LAN implementations at speeds up to 10 Mb/second.

Bluetooth is an alliance between mobile communications and mobile computing companies to develop a short-range communications standard allowing wireless data communications at ranges of about 10 meters. Bluetooth encompasses both a standard communications interface and a low-cost computer chip. It is a cross between the DECT (Digital European Cordless Telephone) and iRDA (infra Red Data Association) technologies. Bluetooth does not involve mobile network transactions as its spectrum is freely available to use in the unlicensed spectrum area (2.45 GHz). Data transmission speeds using Bluetooth are expected to be between 720 kbps and one megabit per second (Mbps). Bluetooth will facilitate WLAN in which networks of different handheld computing terminals and mobile terminals can communicate and exchange data, even on the move and when there is no line-of-sight between those terminals. Bluetooth technologies are designed to be functional even in very noisy radio environments, and Bluetooth voice transmissions are audible under severe conditions. Applications can include pagers, wireless phones, VTC, normal data, e-mail, and web streaming for continuing medical education. One possible use of Bluetooth to implement the invention is for inexpensive high bandwidth communications within the physician's normal work locations and while at home.

Code Division Multiple Access (CDMA) High Data Rate (HDR) provides a spectrally efficient 2.4 Mbps peak rate in a standard 1.25 MHz channel bandwidth for fixed, portable and mobile applications. Optimized for packet data services, HDR incorporates a flexible architecture based on standard IP. HDR is an evolution of CDMA technology with identical radio frequency characteristics as cdma2000 Ix. HDR supports e-mail, web browsing, mobile e-commerce, telemedicine and many other applications while offering end users continuous, untethered, always on access to the Internet and next-generation data services. QUALCOM and LUCENT have announced plans to market High Data Rate (HDR) Code Division Multiple Access (CDMA) based cell phone IP networking in the near term. One possible use of this technology in implementation of the invention is to provide remote and long distance LAN-like access to IP networks that Bluetooth will provide locally.

An exemplary embodiment of the invention used to provide a context for the description appearing below employs both wireless Personal Data Assistant (PDA) and laptop configurations (where appropriate) (or other types of mobile computing devices) at a fixed military medical center and at one or more deployable medical treatment facilities and with forward first responder military medics. The mobile computing device allows point-of-care data-entry, untethered reach-back capability, beaming to support and share medical information with the overall system. A digital medical record with the digital U.S. field medical card DD Form 1380 (DFMC), for encounter documentation and an auto-entry casualty-feeder card. The digital medical record supports accurate casualty reporting, data collection, and medical re-supply information. This information can be downloaded from the mobile computing device wirelessly to a network server or to a flash memory card device which can be given to the patient and viewed on any computing device with a standard browser (e.g. Netscape, Microsoft Explorer, etc), thus providing data integrity, real-time (if communications are available) and near real-time (when communications become available) patient visibility, and automated request for supply based on the injuries reported. In addition, the mobile computing devices in conjunction with the overall system provide a longitudinal digital medical record across the spectrum of care. Integration of the medical record and telemedicine applications with the high capacity Personal Information Carrier, which can serve as the memory device to transport the digital medical record with the patient from the point-of-care back through the various layers of medical care and treatment.

An alternative embodiment adds web-based Internet Protocol and Wireless Application Protocol access to the information contained in the medical records at higher echelons of care to the exemplary embodiment. This information can be made available for medical command, control, and situational awareness, providing real-time decision-making support.

An exemplary way for communication to occur between the mobile computing device and the rest of the system is as follows. A full service two-way data communications in the range of 500 kilobits per second to 2 megabits per second within the physicians normal work environment (office, clinic, hospital) and remotely anywhere that is serviced by digital cell phone Internet access capability. This communication arrangement can take advantage of several existing and emerging wireless technologies to augment current PDA wireless capabilities to deliver full duplex high bandwidth data communications to the palmtop PDA.

The invention in one embodiment preferably includes clinical decision support analysis tools. Examples of possible tools include an electronic medical library allowing real-time access to medical information such as the Merck-manual, Physicians Desk reference (PDR), medical library, and sick-call algorithm books on compact flash memory cards. Another example is the incorporation of intelligent agents and neural net technology into the system, to provide for casualty management support, through the wireless interface. The user could request for medical evacuation (medivac) through a drag and drop graphical user interface or utilize an automated request for evacuation based on cases reported, and receive confirmation and estimated time of arrival based on available assets. Another example is digitizing information contained in a Leaders Book, which provides immediate access to soldier information, pre-deployment checklist, family care plan, next-of-kin notification, and grouping of this information by unit, company, and squad. Other information that may be found in a Leaders Book includes soldier demographics, pertinent medical information, physical profiles, and individual soldier information. In at least one implementation, this would allow immediate access to drop box name fields, and auto-entry of casualty information into the electronic field medical record as well as the casualty feeder card.

The exemplary embodiment could be implemented to include digital training tools for Continuing Medical Education tools and/or games such as Expert Field Medical Badge (EFMB), jeopardy, hangman, or who wants to be a medic word game. The games could utilize medical terminology, EFMB or National questions. The games can be single player, and multi-player. Results could then be stored and used to train individuals using these tools to improve their level of proficiency.

The invention preferably includes a system for providing longitudinal medical records for patients including, for example, medical history, prior examinations, injuries, health events, etc. The system preferably, in further embodiments, includes mechanisms for requesting dispatch of transportation for the patient, ordering of supplies for the first responders and other medical facilities, recording of information relating to pre and post deployment of armed forces (or other work forces where this type of medical information would be of assistance). Although the exemplary embodiments described below relate to the armed forces, one of ordinary skill in the art will understand that this system can be implemented in a civilian application where, for example, in place of medics there would be first responders, in place of medvac there would be civilian air transport such as the various life flights, in place of battalion aid station or other medical facility would be a hospital, etc.

FIG. 1(a) illustrates an exemplary embodiment of the invention that shows a generic computer network 102, a plurality of mobile computing devices (mcd) 104, at least one database 106 at a medical facility such as a hospital. The plurality of mobile computing devices 104 as illustrated are positioned with the first responders to the injury. The mobile computing devices 104 also could be available to medical professionals at the hospital as illustrated in FIG. 1(b), which facilitates a common tool for entry of information into the system to create the longitudinal medical record.

FIG. 2 illustrates an exemplary embodiment of the invention where the system includes a plurality of mobile computing devices 104; a plurality of computer readable material such as floppy disks, PICs, flash memory, etc. 108; at least one database 106; and a network 102 connecting some of the mobile computing devices to the at least one database. This exemplary embodiment is illustrative of an implementation in which the mobile computing devices 104 with first responders are not connected to the at least one database 106 during a response to situs of the point-of-care. However, the information recorded in the mobile computing device 104 may be transferred via computer readable material 108 (i.e., a sneaker net) to a computer or other mobile computing device 110 attached to the network 102 to transfer the information to the database 106 or, alternatively, once the mobile computing device 104 with the first responder is able to establish a network connection transferring the information to the database 106 without resort to a sneaker net.

FIG. 3 illustrates an exemplary embodiment that blends the exemplary embodiments illustrated in FIGS. 1(a)-2. FIG. 3 illustrates a portion of a system having a plurality of mobile computing devices 104, a plurality of communication nodes 112, at least one database 106, and a network 102 connecting the communication nodes 112 to the database 106. There may also be multiple computers 110 connected to the database 106 for accessing the health status of individuals present in the system. The embodiment illustrates that health information is recorded on a mobile computing device 104 and is transferred to a communication node 112. The mechanism for transfer can be accomplished using a variety of connections 114 including, for example, computer readable medium, a wireless connection, a direct connection between the mobile computing device and the communications node, and/or a wired connection. The communications node 112 can be, for example, a secured laptop with a network connection (such as satellite or radio), a communication radio (such as a two-way radio or modem), and/or a satellite telephone.

This exemplary embodiment is particularly useful at the present time for more securely transmitting medical information than what is reasonably obtainable using PDAs, which as referenced above may be the mobile computing device. The communications node is more capable of securing the transmission because of processing power and other capabilities of, for example, a laptop computer. In this more particular exemplary embodiment, information could flow from the PDA to the laptop computer via computer readable memory and then from the laptop computer to the network and to a database that is remote from the laptop computer. Once the information is resident in the database, leaders/commanders may access the information to learn the current health status of their work force such as military forces. This information also allows for medical surveillance, in transit visibility, casualty reports that may be used by leaders/commanders, medical professionals awaiting transit of patients, etc.

The invention preferably includes software that is flexible enough to allow it to be portable between handhelds like PDAs (more particularly the Compaq iPAQ), laptop computers, desktop computers, and other types of mobile computing devices. Software written in C++ and using XML for the information is easily portable between at least some PDAs and larger computing devices like computers (laptop and/or desktop). What follows is a description of exemplary components for use as part of the software. The software preferably includes components that allow for entry of information regarding the patient and transferring that information to other computer readable medium and/or to a computer network for submission to at least one database connected to the computer network.

FIGS. 4-23(e) illustrate an exemplary embodiment of the software interface for use on the mobile computing devices and these Figures illustrate screen layouts setup for PDAs. FIG. 4 illustrates an exemplary startup screen that has a variety of buttons for starting different software components that would be useful in this invention. The "X" 401 in a circle in the upper right-hand of the screen minimizes the screen for this particular screen; however, the "X" serves as a back/cancel button on the screens after the start-up screen. The select patient field 402 is for selection of a previously entered patient from in this embodiment a dropdown list. The selection of a particular patient in the select patient field 402, provides a starting set of information for any of buttons relating to medical records (buttons 404-418). The add button 404 opens an interface to add a new patient or edit an existing patient (if a patient has been selected in the dropdown list). The Readiness button 406 allows the user to view the selected patient's readiness information. The DD 1380 button 408 allows the user to start a Field Medical Card (SF 1380) for the selected patient. The Encounter button 410 allows the user to start a sick call encounter for the selected patient. The SF600 Encounter button 412 allows the user to begin a SF600 encounter for the selected patient. The Exam button 414 allows the user to review and/or start an examination report for the selected patient. The Reports button 418 allows the user to start a report regarding the selected patient. The Encounters field 420 provides a running tally of the number of encounters entered in with this unit since the counter has been reset. The provider information is shown in area 422. The Exit button 424 quits the program. The Tools menu 426 allows the user to adjust the system settings for the software.

Figure 5B:
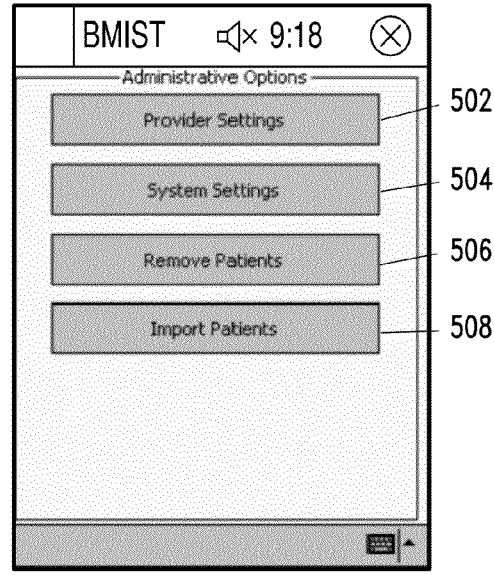
Figure 5A:
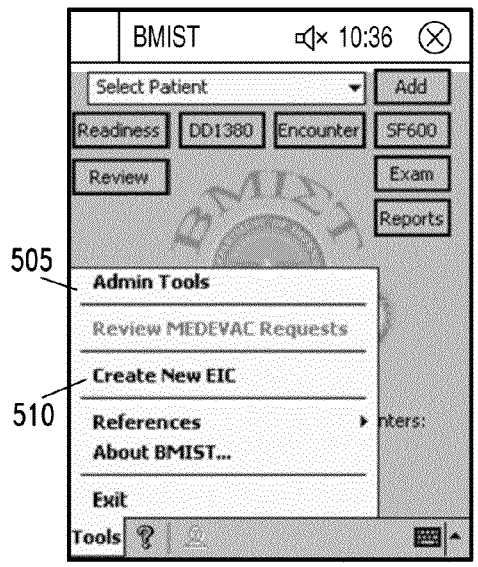

The user is able to access a variety of administrative functions through selecting the administrative tools item on the Tools menu as shown in FIG. 5(a). The administrative options as illustrated in FIG. 5(b) include a Provider Settings button 502, a System Settings button 504, a Remove Patients button 506, and an Import Patients button 508.

Figure 6:
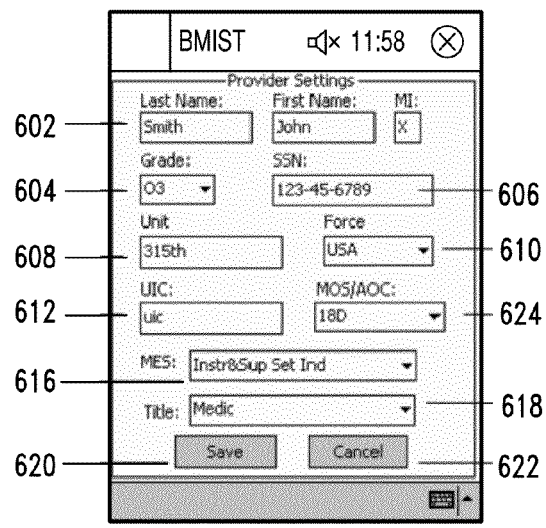

When the user selects the Provider Settings button 502, the user is provided with the interface shown in FIG. 6. The text fields 602 are for the provider's first name, last name, and middle initial. The provider in this exemplary embodiment would be a medic that has been assigned this particular mobile computing device. Other demographic information is provided in the system like, pay grade (field 604), social security number or other identifier (field 606), unit identification (field 608), force identification such as U.S. Army, U.S.

Navy, civilian, etc. (field 610), unit identification code (field 612), the user's military operational specialty (MOS) (field 614), identifier of the medical equipment set (MES) assigned to the user (field 616), and the user's title (field 618). This exemplary embodiment also shows a combination of drop-down menus and open text fields depending upon the information needed for a particular field. Also, the MOS and MES will impact some of the intelligent operation of the system including treatment options and/or recommendations including type of drugs to administer. The Save button 620 and the Cancel button 622 are typical buttons to activate, respectively, saving of the settings and canceling any changes made to the settings.

Figure 7A:
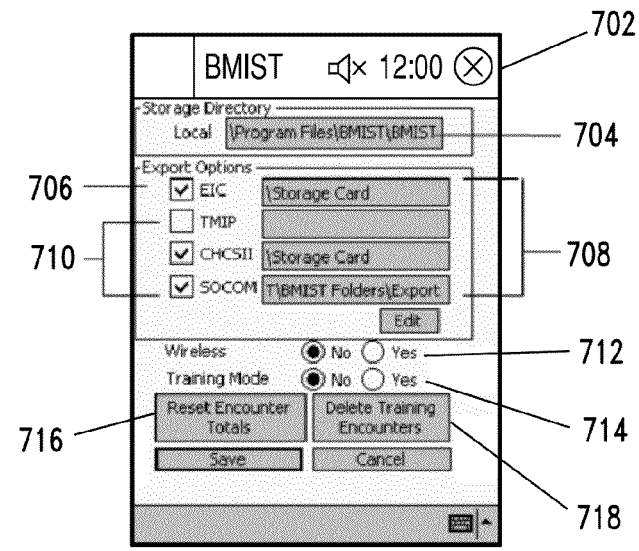
Figure 7B:
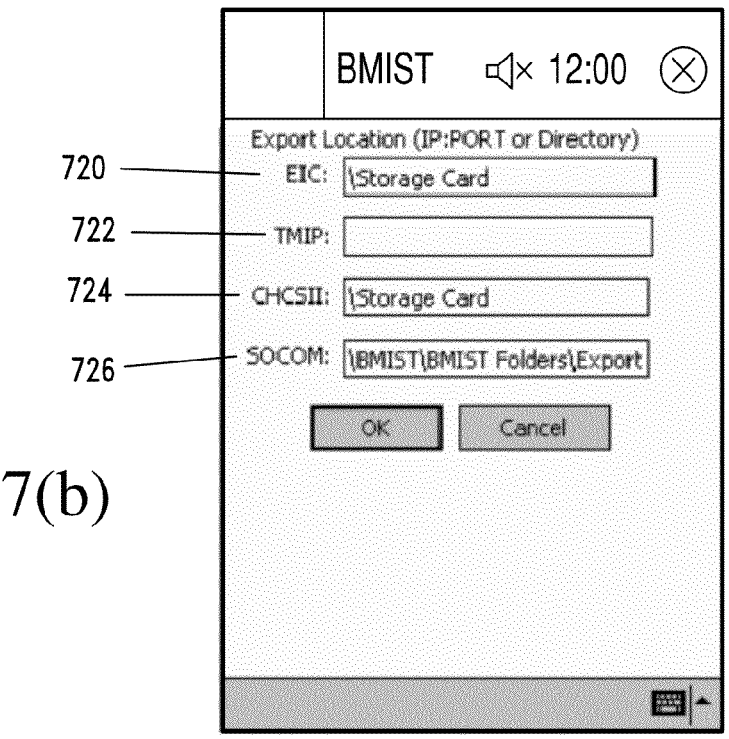

The user is able to change the system settings by selecting the System Settings button 504 in FIG. 5(*b*), which is opened by selecting the Admin Tools option in the Tools menu illustrated in FIG. 5(*a*). The system settings screen is illustrated in FIG. 7(*a*). This screen allows the user to adjust and review different system options such as file storage locations, wireless capabilities, and export options. The "X" button 702 will return the user to the administrative tools screen shown in FIG. 5. The local storage field 704 provides the location for the local storage directory for the software. The export options include checkboxes 706 and 710 and text fields 708. A particular export option is enabled if the corresponding checkboxes 706 and 710 is selected. The text fields 708 provide the absolute directory for each export option, the system is designed to retain information being exported when there is no connection available to export the information so that if at a later time the connection becomes available the export may occur. An alternative to entering a directory is using the IP address (or other network name nomenclature) for a particular database. The exemplary embodiment is designed to allow export of information to the PIC (or Electronic Information Carrier (EIC)), TMIP, CHCSII, and SOCOM. The EDIT button allows the user to edit the text fields 708. Selection of the EDIT button brings up a screen similar to that shown in FIG. 7(*b*) that allows the text fields 708 to be edited; however, these functional steps could be omitted and instead type the file locations right into the text fields 708. This exemplary embodiment uses the My Device folder as the relative base for the rest of the locations, such that the My Documents folder has a location/My Documents.

The user is able to enable and/or disable the wireless capabilities depending upon the radio button selection at 712. The exemplary embodiment also includes a training mode 714 that may be enabled. The Reset Encounter Totals button 717 resets the total and pending encounter counters. The Delete Training Encounters button 718 works in conjunction with the training mode and is used to erase records during training by the user.

This exemplary embodiment is able to export data to EIC, TMIP, CHCSII, and SOCOM. There is a variety of ways for the medical information to get these different databases from the mobile computing device. The medical information also will be maintained on mobile computing device after the transfer in this exemplary embodiment. CHCSII may receive the exported files through, for example, EIC or via ActiveSync. The EIC transfer method allows the user to load the medical information for a particular patient onto the patient's EIC card, which will need to be inserted into an adapter attached to the mobile computing device at some point to receive the medical information. This transfer method is accomplished in the exemplary embodiment by setting the CHCSII field to the location where the storage card is, i.e., \Storage Card, as illustrated in FIG. 7(*b*).

If the information is to be transferred to CHCSII via ActiveSync, then the export location is changed to "\My Documents" to facilitate the information being synchronized. When it is time to transport the information the mobile computing device, which in this exemplary embodiment is a PDA (or the mobile computing device) is inserted into a cradle to be synchronized with a host computer.

The transfer method for SOCOM is the information to be transferred is stored in an Export directory on the PDA until it is transferred. See, e.g., FIG. 7(*b*). The files that are created to facilitate the export then are manually copied over as part of an ActiveSync process to the host computer for sending to the relevant database. The files residing in the Export directory containing the transferred information also need to be deleted after the transfer to prevent duplicate information being sent to the database.

The information to be exported from the PDA is stored in XML to facilitate easier transfer into the designated databases.

Figure 8:
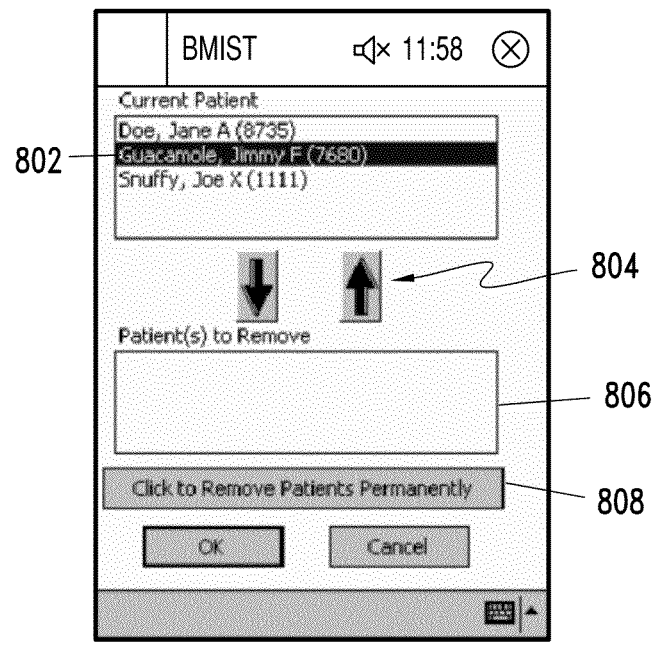

The Remove Patients button 506 in FIG. 5(*b*) brings up the interface shown in FIG. 8 that allows the user to remove patients from the database. Reasons that might exist for removing a patient include the user no longer needs to keep track of the patient or there is no reason for medical information about the patient(s) to still be resident on the PDA. The Current Patient window includes a list of patients whose data currently is available on the mobile computing device. The arrow keys 804 allow the user to click on the appropriate arrow to move someone from one window to the other window. The Patient(s) to Remove window 806 displays any patient who has been selected to be deleted from the database on the mobile computing device. Patients are transferred from one window to the other by clicking and selecting the patient's name. Once the list of patients to be deleted is completed, the user then clicks on the Click to Remove Patients Permanently button 808 to remove the patients from the local database on the mobile computing device.

The Import Patients button 508 in FIG. 5(*b*) brings up the interface shown in FIG. 9(*a*) that allows the user to manually add a new patient record into the database on the mobile computing device. The first step if the patient information is coming from a file is to either type in the absolute file path and filename into the textbox 902 or click on the Select File button 904. Clicking on the Select File button 904 will produce a list of *.xml files on the device as illustrated in FIG. 9(*b*). The user then can select the file to import by tapping on the filename, which will then insert the absolute path and filename for the selected file into the textbox 902. To complete the import of the patient, the user hits the Import button 906, which will complete the importation and in this exemplary embodiment provide an indication to the user of the number of patients imported as illustrated in FIG. 9(*c*). The exemplary embodiment is setup to import only the demographic information and not patient encounters; however, this could be changed for a different implementation and still be within the scope of this invention.

The exemplary embodiment also allows two devices to share patient data using the following method. On the source device, the user enters the file exploring utility to browse to the location of the patient list file (e.g., patList.xml). Once the file is located, the user should select and hold the file until a pop-up menu appears to allow the user to select copy (or other ways to copy the file that are well known may be used). The user then needs to browse to the transfer medium such as a storage card and paste the file there. The user then removes the transfer medium, which is then inserted into the destination device. At the destination device, the import file steps discussed above are used.

The method to import a file from CHCSII is similar in that once the file is on a transfer medium and that medium is inserted into the destination device the import steps discussed above are followed. Typically the CHCSII import file names will be something like CHCSIIT_BMIST*.xml. An example of the contents of a CHCSII import file is shown in FIG. 9(b). One of ordinary skill in the art will appreciate that XML documents may be created from a variety of other document types using export functions such as from an Access database assuming that the columns in the table are named to correspond to what is illustrated in FIG. 9(b). If a patient that is being imported into the device already is present in the local database (based upon, for example, the same social security number), then the demographics of the patient will be updated.

The exemplary embodiment has another way to import patient information, and that is via an EIC. This importation occurs when a communication link is established between an EIC and the mobile computing device, most likely through a reader attached to the mobile computing device that is designated in the system settings. The software checks to see if the patient to whom the EIC belongs is already in the current patient list. If the patient does not exist in the list, the patient and all his demographics are automatically imported. If the patient already exists (determined for example based on a matching social security number or other identification number), only the demographical information for the patient is updated along with any readiness file that might be on the EIC. A notification message is displayed for the user if the patient was imported successful as illustrated in FIG. 9(c). This all assumes in this embodiment that the EIC has been properly initialized and formatted for the patient.

The Tools menu also includes a Create New EIC option for this exemplary embodiment. The first step in creating (or formatting or initializing) a new EIC is to select a patient from the patient field to export to the EIC. The next step (although these two steps could be reversed) is to insert an empty EIC into the device. The third step is to select "Create New EIC" from the Tools menu, which then will prompt the device to format the EIC for the selected patient including, for example, the patient's demographic information along with his/her readiness file. Once the process is finished a message box will appear to verify success or to notify the user there was an error. Sources of an error are failure to select a patient, the EIC already has another patient's information, or no EIC was inserted.

Figure 9A:
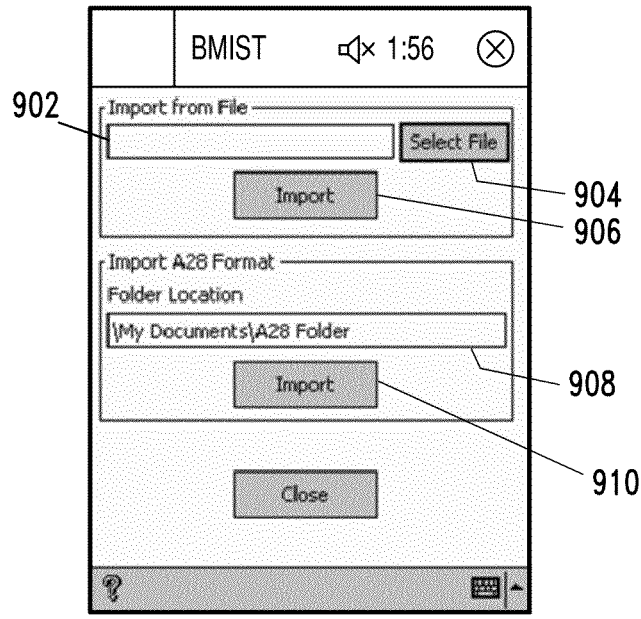
Figures 11A, 11B, 11C:
Figure 11D:
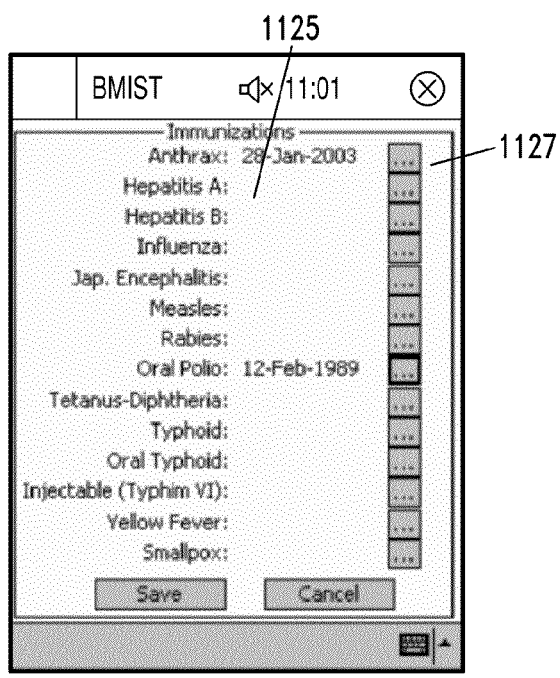
Figure 12A:
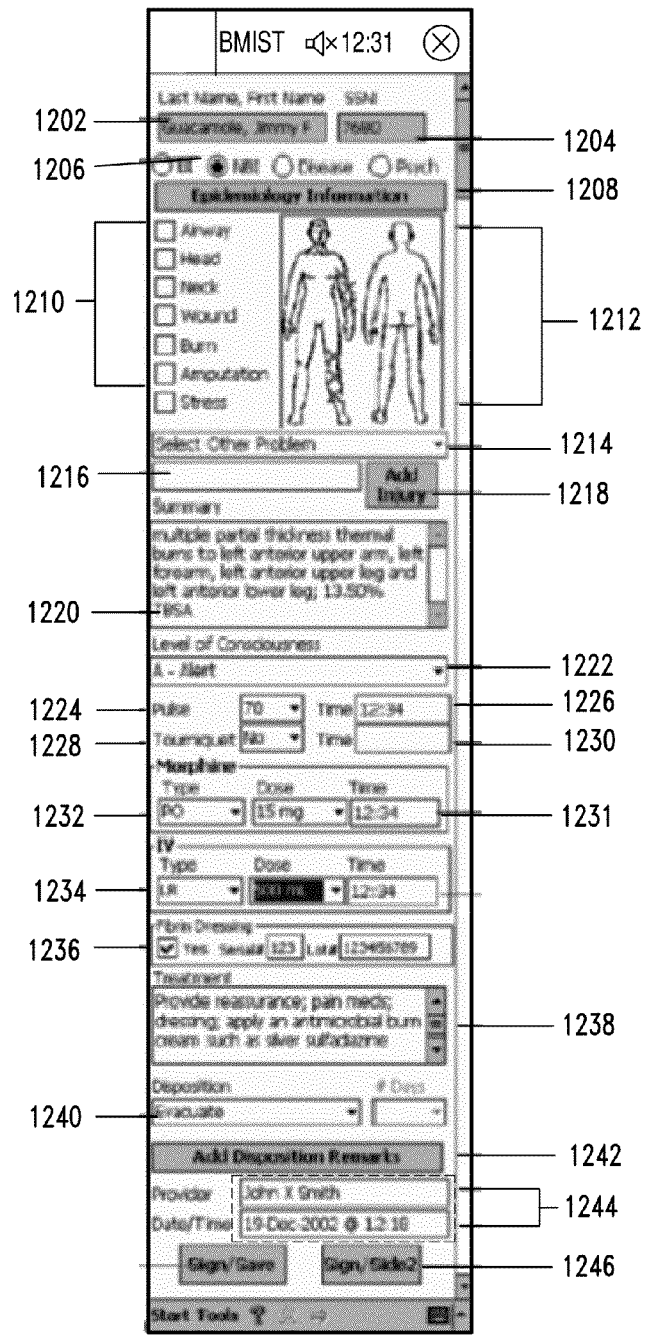
Figure 12B:
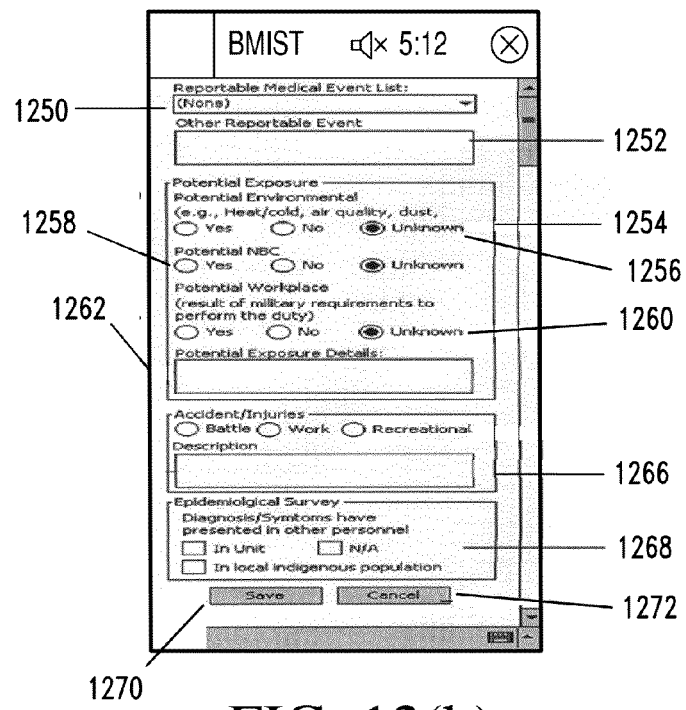
Figure 12C:
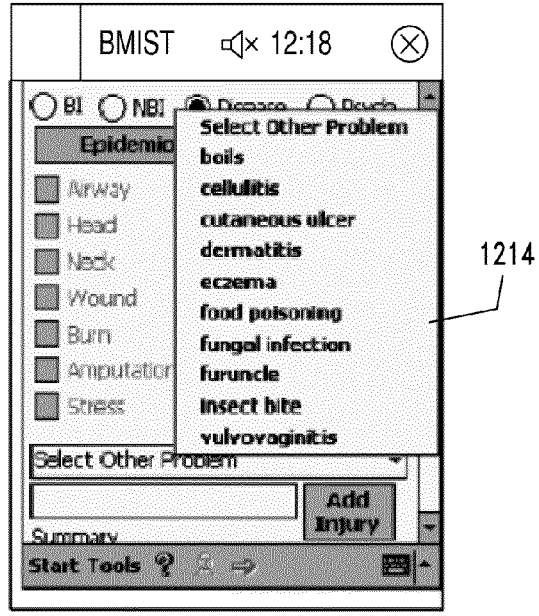
Figure 12D:
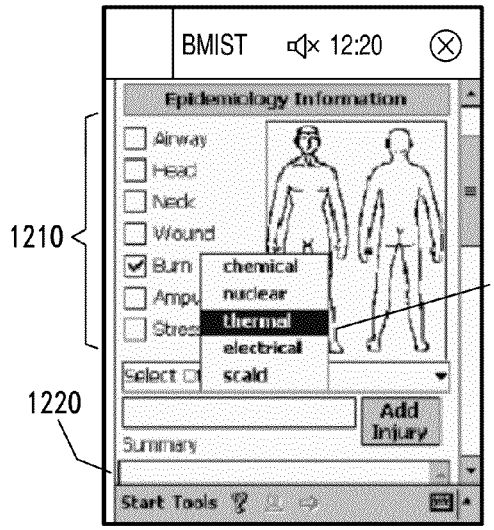
Figure 12E:
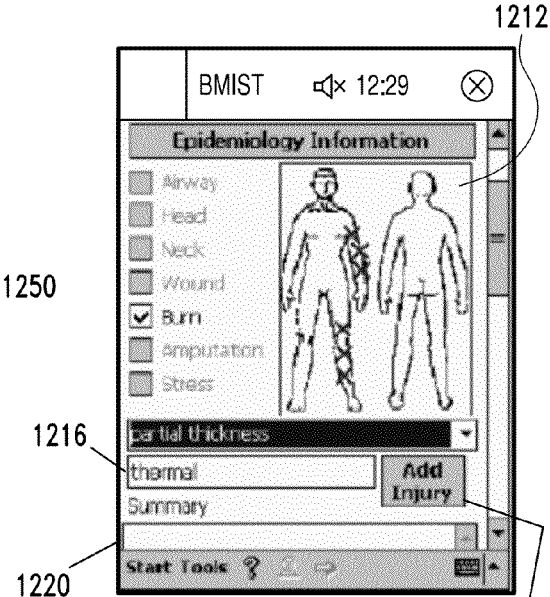
Figure 12F:
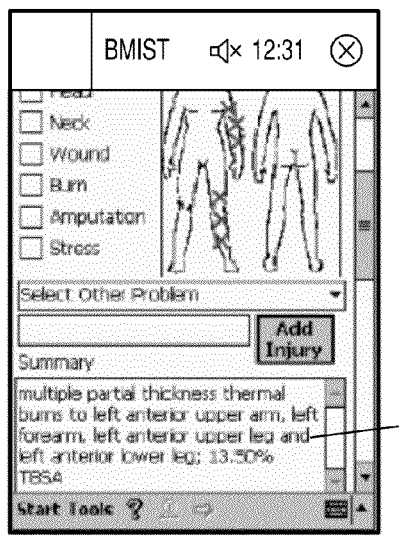
Figure 12G:
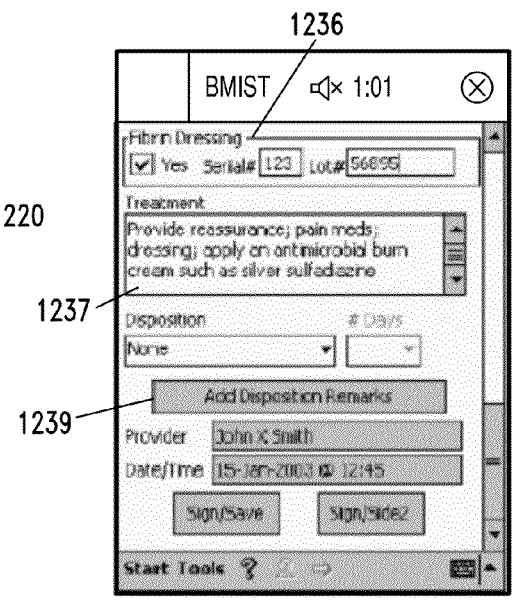
Figure 14A:
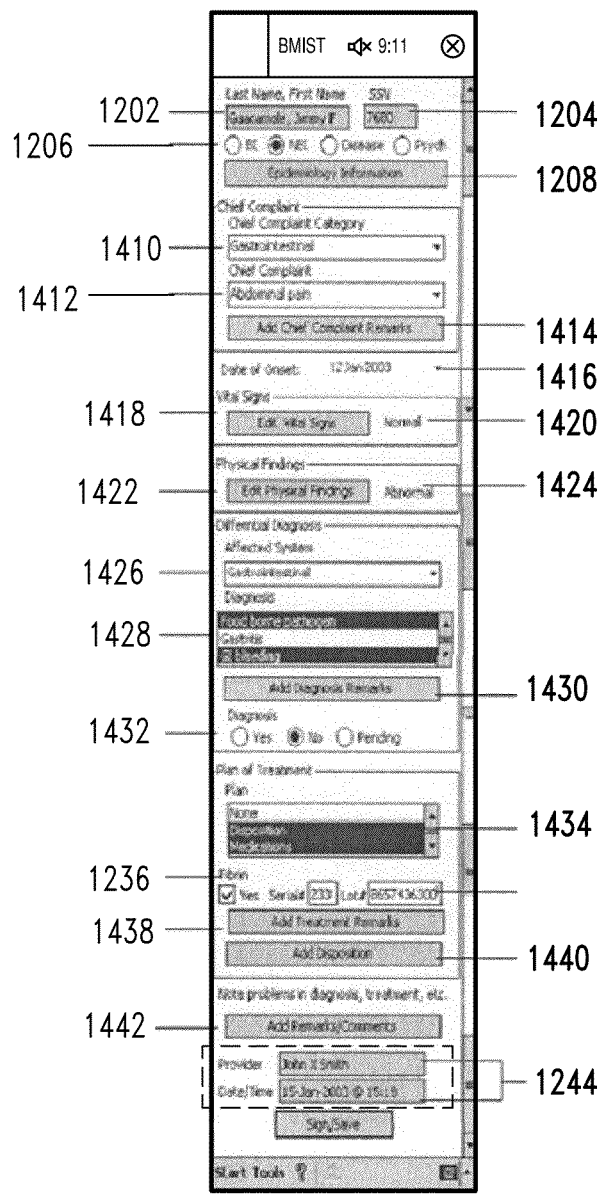
Figure 14B:
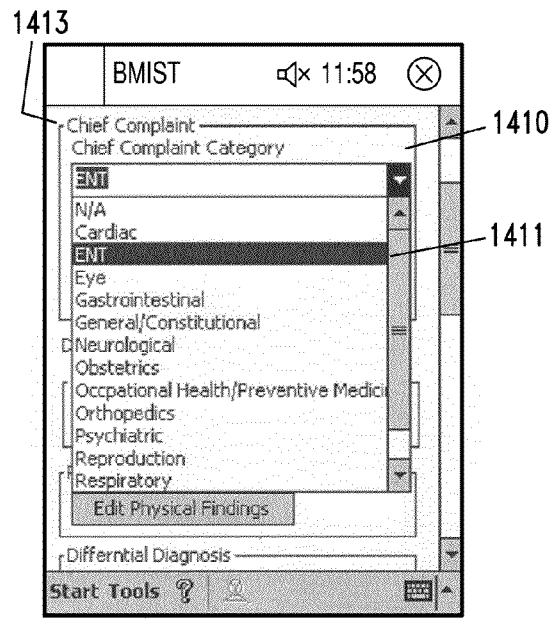
Figure 14C:
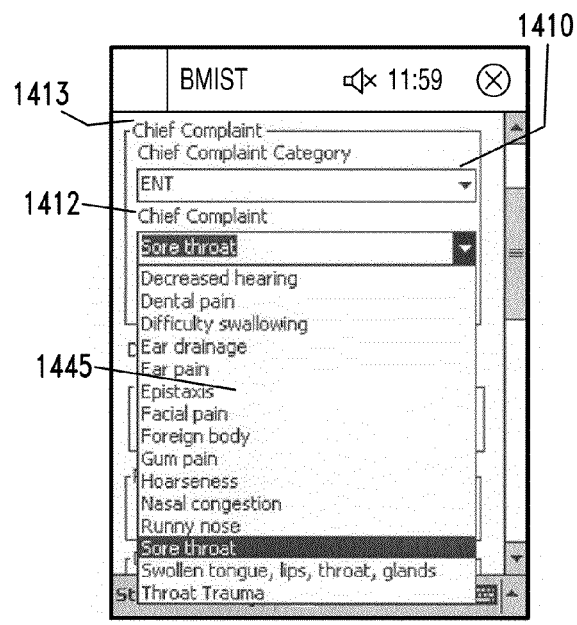
Figure 14D:
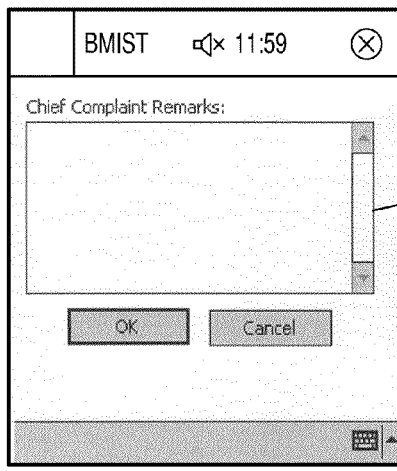
Figure 14G:
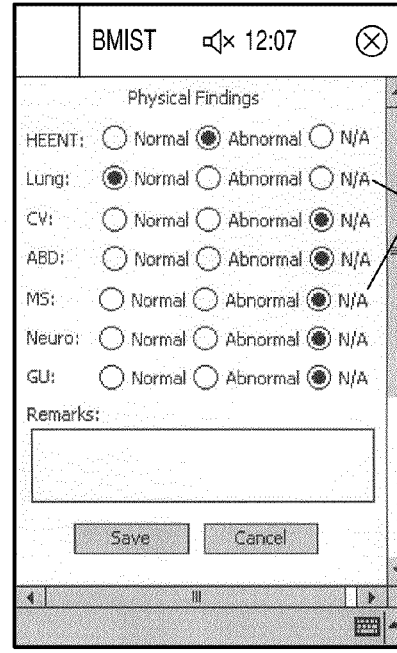
Figure 14E:
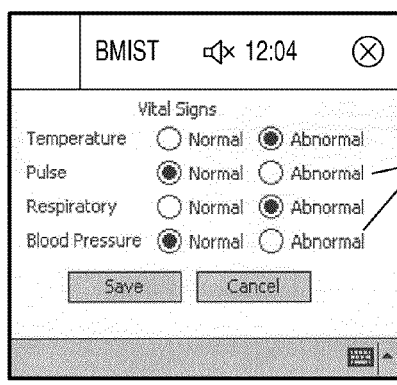
Figure 14H:
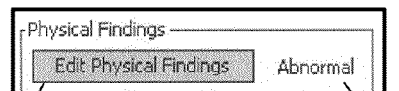
Figure 14F:
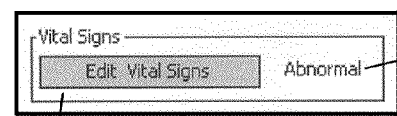
Figure 14I:
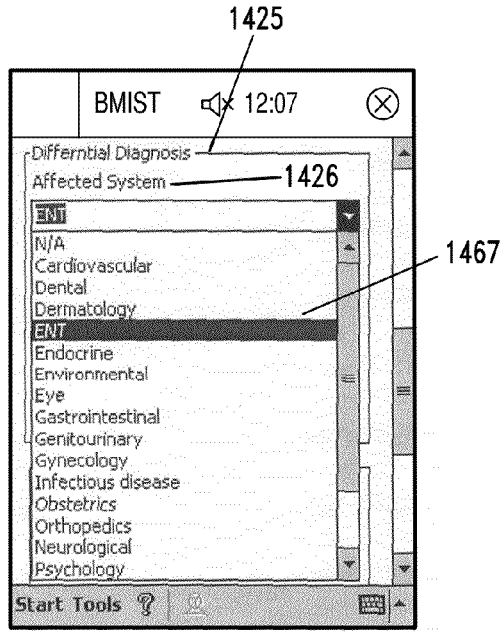
Figure 14K:
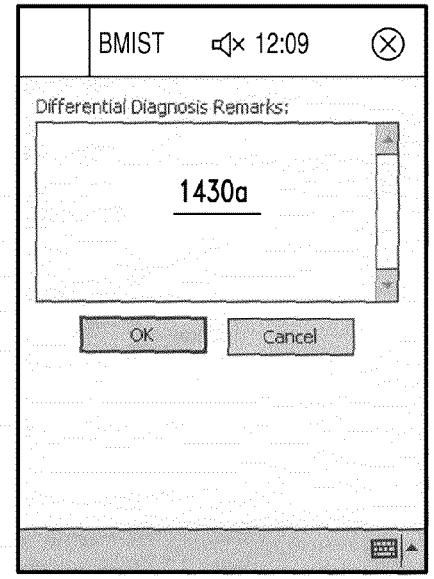
Figure 14J:
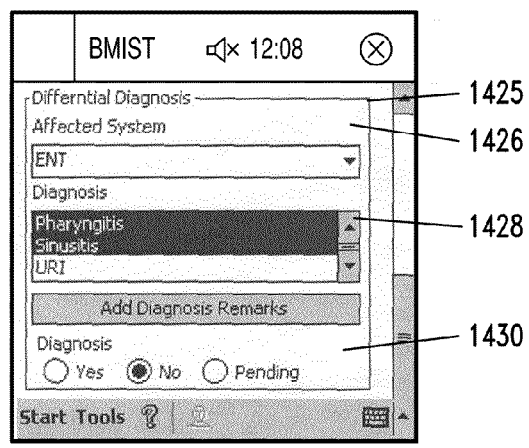
Figure 14L:
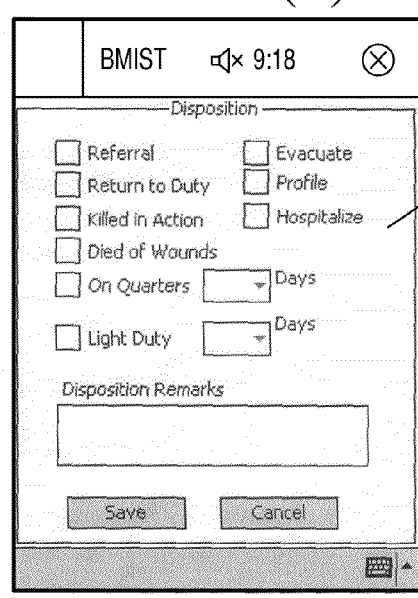

FIG. 9(a) illustrates an Import A28 Format section. This portion of the interface can be used to import files that are in the A28/HL7 format. These types of files typically would be exported from the TMIP architecture into a predetermined folder on the destination device such as the My Documents directory. The device then goes to the folder location entered in the folder location field 908 once the Import button 910 is clicked by the user. The device then will attempt to import all *.xml files in the directory, and once the processing is completed all of the XML files will be deleted from the directory irrespective of whether they were successfully imported.

In order to begin the encounter process or review medical information, a patient must be selected in the select patient field 402. Or alternatively, if the patient is listed and there is no EIC from which to upload information, then the user may add a new patient to the database on the device. The exemplary embodiment provides two ways to select a patient: manually and automatically. To manually select a patient, the user pulls down the dropdown menu listing each patient in the device database by last name, first name, and the last four digits of the social security number. The user scrolls through the list to locate the patient's name and selects it. To automatically select a patient, the user inserts the patient's EIC into the device reader and the device will auto select the patient based on the contents of the EIC. The exemplary embodiment is set-up to deselect the patient if the EIC is withdrawn while the user is at the startup screen.

The exemplary embodiment allows a patient to be added from scratch by selecting the Add button 404. When this button is selected a blank form similar to what is reproduced as FIG. 10. The form provides for entry of a patient on which the user has no information, i.e., the Unknown Patient button 1002. If the user has information regarding the patient either through personal knowledge, another information source, or the patient; then there are a variety of fields that may be completed, for example, name and sex fields 1004, patient's blood type and Rh factor field 1006, social security number or other identifier field 1008, height and weight fields 1010, a date of birth field 1012, a nationality field 1014, a race field 1016, a religion field 1018, a force (or branch of service) field 1020, a grade field 1022, a rank field 1024 (that may be automatically completed if both the force and grade fields are completed), a unit name field 1026, a specialty field 1028, a MOS/FAD field 1030, a mission name field 1032, a unit identification code (UIC) field 1034, a geolocation field 1036, and a country field (for where the patient is deployed) 1038. The fields may be a mixture of dropdown menus and open text fields. Depending upon the mission, some of the fields may be stripped of information during the transfer to a central database and/or be coded such that if the security of the device was breached there would be a minimization of incriminating information.

The selection of the Unknown Patient button 1002 will populate the name and social security fields 1004 and 1008 with information. The name fields 1004 will be completed based on the entered sex of the patient with John (or Jane) Doe (1) with the (1) being incremented if there are multiple Does. The generated social security number is XXX-XX-XXXX. If the user learns additional information about the patient, then the user can edit the patient record to reflect the learned information.

If the patient is known, but information regarding the patient is classified, then a code system may be used to enter information regarding the patient. The exemplary embodiment allows entry of a code that automatically disables the first name and social security number fields to prevent accidental entry of information into these fields based on the code being entered into the last name field.

As indicated above, it is possible to edit an existing patient record to correct and/or update information regarding the patient.

The exemplary embodiment has a variety of forms and data entry mechanisms to record medical information relating to a patient. FIGS. 11(a)-(d) illustrate a data entry interface for entering and viewing previously entered information relating to the patient's readiness that is obtained by selecting a patient and clicking on the Readiness button. Fields 1102 show the patient demographics, which are automatically populated in this exemplary embodiment based on the patient information when this data entry interface is first accessed for the patient. The flight status fields 1104 are a set of dropdown boxes for flight status, flight rating, and personal reliability program (PRP) values for personal. The set of PULHES boxes 1106 and accompanying date are for entry of ratings for physical capacity or stamina (P), upper extremities (U), lower extremities (L), hearing including ear defects (H), eyes (E), neuropsychiatric values (S), and the date when these values were entered. The Add Exam Dates button 1108 brings up another screen, shown in FIG. 11(*b*), to enter exam dates. The dental health fields 1110 are for entry relating to the patient's dental records and whether they are ready for deployment from a dental perspective. The allergy list 1112 allows entry of common allergies that the patient has by selecting all of the relevant allergies. If for some reason the patient has an allergy not listed, then the Other textbox 1114 can be used to type out the allergy not listed. The medical warning tag box and accompanying date field 1116 is for entry of whether the patient has such a tag and when it was issued. The Glasses section 1118 is for a quick notice regarding whether the patient has glasses and includes an Edit Glasses button for displaying the interface shown in FIG. 11(*c*). The Immunization Dates and Dosages section includes an Edit Immunizations button 1120 that when clicked displays the interface shown in FIG. 11(*d*). The Chemoprophylaxis section 1122 is for entry of information relating to this type of treatment including disease name, medication, and dosage in table format although other display arrangements could be used. The Current Medical Condition/Medications section 1124 allows entry of multiple conditions and medications and the Other Medications field 1126 is available for entry of a non-listed condition and/or medication. The last field is a Remarks field 1128 for entry of any additional remarks that may be useful and/or informative regarding the patient.

FIG. 11(*b*) illustrates a list of readiness exam dates that is accessed by selecting the Add Exam Dates button 1108 in the interface shown in FIG. 11(*a*). The user is able to click on the dropdown dates to enter the dates for the listed examinations. The PAP Exam and Results are only enabled if the patient was entered as a female patient. Alternatively, other combinations of examinations could be listed in this interface.

FIG. 11(*c*) illustrates an interface for entering eye glasses information. Part of the reason for inclusion of this screen is that during deployment in the early 1990s, U.S. Armed Forces were expending monies to bring troops out of deployment positions to replace lost and/or damaged glasses. However, with eye glass information entered into the system prior to deployment, a new pair of glasses could be ordered and sent to the soldier in the field without the need to bring the soldier rearward for an eye examination. As a result, the interface includes the basic information that would be contained on a regular vision prescription such as sphere, cylinder, axis, add, HT, and PD for each eye along with a textbox for temple length.

FIG. 11(*d*) illustrates an interface for entering immunization information for the patient. This interface allows entry of the various immunizations that may be required prior to deployment with each immunization having a ". . . " button to be clicked to allow entry of the date the immunization was given to the patient. This particular exemplary embodiment allows entry of dates for Anthrax, Hepatitis A, Hepatitis B, Influenza, Japanese Encephalitis, measles, rabies, oral Polio, tetanus-diphtheria, typhoid, oral typhoid, injectable Typhim VI, Yellow Fever, and smallpox.

FIGS. 12(*a*)-15 illustrate the interfaces related to entering information about an encounter with a patient including the use of the field medical card, reassessment, sick call encounter, and form SF600. Each of these encounters serve as examples of the type of information and flexibility that is possible with the mobile computing devices according to the invention. Each of these interfaces includes a scroll bar when the interface is longer than the screen of the mobile computing device is able to display on one screen.

FIGS. 12(*a*)-(*l*) illustrate how a field medical card would be completed in this exemplary embodiment which also has added components to record epidemiology information and recordation of field use of a dressing being tested as part of human trials. FIG. 12(*a*) shows the interface for completing a field medical card otherwise known as form DD1380, which can be assessed from the start screen by selecting the DD1380 button after selecting a patient. Patient name field 1202 and social security number 1204 are automatically completed based on information contained in the patient record. The Epidemiology Information button 1208 upon being clicked pulls up the interface shown in FIG. 12(*b*).

One or more injuries may be added to the field medical card. Each injury will include type of injury case, type of injury, specific injury, locations, and injury severity. The injury type set 1206 is preset to default to NBI for non-battle injury, but the user is able to change the injury type to battle injury (BI), disease (Disease), and psychiatric (Psych). Additional types of injuries that are not classified as one of these four may be selected using the Select Other Problem dropdown list 1214 as illustrated in FIG. 12(*c*). For the disease and psychiatric injury types, a popup list containing specific problems of that type appears for the user (or provider) to select from. The injury descriptor set 1210 and location of injury drawing 1212 are used to enter the injury suffered by the patient. When an injury descriptor is selected a popup list appears containing specific problems of that injury descriptor as illustrated in FIG. 12(*d*). The selected specific problem will appear in the blank text box 1216 to the left of the Add Injury button 1218. For the injury descriptors that require a location, the user clicks on the picture of the body 1212 to show where the injury occurred as illustrated in FIG. 12(*e*). If an "X" is incorrectly placed, then the user can just click on it to remove it from the body. Multiple locations may be included on the body diagram as illustrated by the six "X"s in FIGS. 12(*a*) and (*e*). The user is able to select the severity of the injury using the Select Other Problem dropdown list 1214 that dynamically changes to a list of appropriate severities from a list of generic injuries discussed above as illustrated in FIG. 12(*e*). If the user needs to add another injury for the patient, then the user selects the Add Injury button 1218 to save the current injury and provide a clean interface to add a second injury. The Summary section 1220 is a description of the injuries that the patient has based upon the selections and locations entered by the user as illustrated in FIG. 12(*f*). As the user enters information, the software correlates ICD9 codes with the information entered by the user. The user may add additional information in the summary box if needed. After all of the injuries are entered, then the user moves onto the next section of the field medical card.

The Level of Consciousness field 1222 is automatically completed based on the injuries entered by the user based on the typical consciousness level that would be exhibited by a similar patient having those injuries. The user is able to change the level of consciousness to accurately reflect the patient's current level of consciousness.

The interface allows the user to enter information relating to what the pulse is 1224 and whether or not a tourniquet was applied 1228. If either of these fields is completed, then the system automatically timestamps the entry for the user. The next two sections relate to morphine given 1232 and an IV being given 1234. The user enters the type and then enters the dosage from a dropdown menu having dosages for the type of morphine/IV given to the patient. The time for both of these is then automatically entered by the system.

The Fibrin Dressing section 1236 is for entry of the use of a fibrin dressing on the patient. This is an example of incorporating the collection of data and information for analysis of the effectiveness of in this case the fibrin dressing. If a fibrin dressing was applied, then the user is to enter the serial number and lot number of the particular dressing applied.

The Treatment section 1238 is automatically completed based on the injury(ies) suffered by the patient and is illustrated in FIG. 12(*g*). The treatment may be tied to the skill and knowledge level of the user along with taking into account the supplies available to the user for treating the patient. The treatment also is based on standard practice guidelines that have been established for treating various injuries. The user may select the disposition 1240 of the patient from a list including deceased, evacuation, returned to duty, hospitalized, light duty, and quarters with the last four allowing the user to enter a number of days. If the user feels additional comments may be of assistance, then the user can click on Add Disposition Remarks button 1242. The provider section 1244 is automatically completed by the system based on the user logged onto the mobile computing device to include their name and a date/time stamp for this encounter.

FIG. 12(*b*) illustrates an interface for entering epidemiology information. This information can be used to assist in analyzing trends that may exist regarding particular injuries and/or illness so that an investigator may be able to more quickly trackdown the source of an injury and/or illness. The system is set-up to automatically populate the interface if any has already been entered, which will assist in expediting the entry of this information. Fields 1250 and 1252 can be used together to enter the medical event that occurred and to which this report is being attached. The Potential Exposure section 1254 solicits information relating to the environment at the time of the health event including an open text field. The Accident/Injuries section 1256 solicits information regarding particulars about the source of the injury. The Epidemiological Survey section 1258 requests information relating to whether the diagnosis and/or symptoms have been present in other individuals in the patient's unit or the surrounding civilian populace.

Figure 13:
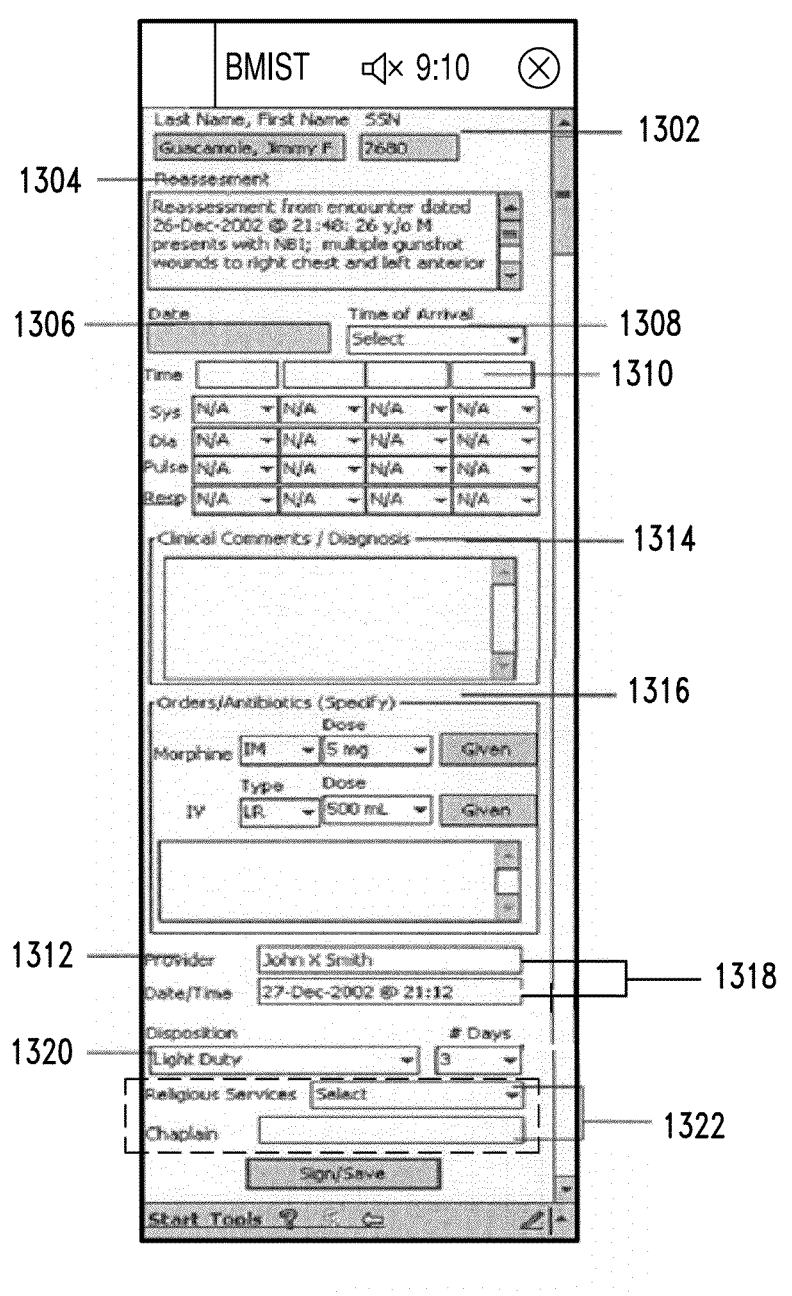

The reassessment of a patient can occur a couple of ways either by clicking on the Sign/Side 2 button 1246 on the field medical card or the Reassess-Add button on the start screen after selecting the patient. FIG. 13 illustrates a reassessment side of the field medical card. The name and social security number of the patient 1302 are automatically populated. The Reassessment textbox 1304 and Date field 1306 is populated with information taken from the encounter detailed on the virtual front side of the field medical card. The Time of Arrival field 1308 provides the user the change to enter that information if the patient has been transported. The reassessment time and vitals fields 1310 and 1312 include a set of four time, systolic blood pressure (Sys), diastolic blood pressure (Dia), pulse (Pulse), and respiratory (Resp). This information could be manually entered by the user, pulled on demand from sensors attached to the patient, or automatically pulled from sensors attached to the patient at set time increments and/or if triggered based on a preset number(s) for at least one vital sign. This exemplary embodiment is set up to enter the time when vital signs are entered by the user.

The Clinical Comments/Diagnosis textbox 1314 is for entry of additional comments and diagnosis based on the reassessment by the user. The Orders/Antibiotics (Specify) section 1316 allows for entry of further doses of morphine and IV similar to how the dosing was entered in for these two during the initial encounter, for example, see fields 1232 and 1234 in FIG. 12(*a*). There also is a textbox for entry of other types of orders and/or antibiotics. The Provider section 1318 is automatically completed based on the provider information in the system for the user. The disposition section 1320 is similar to the disposition section 1240. If religious services are desired and/or necessary, then this can be noted in the Religious Services section 1322.

FIGS. 14(*a*)-(*l*) illustrate interfaces for performing a sick call encounter of a patient by the user (or provider). From the start screen, the user clicks on the Encounter button. The sick call encounter interface shares the patient name and social security fields 1202, 1204, sick call type 1206, Epidemiology Information button 1208, and provider section 1244 with the field medical card interface shown in FIG. 12(*a*). This encounter interface also shares the Fibrin section 1236 with the field medical card interface shown in FIG. 12(*a*), which could be omitted and/or replace and/or augmented with some other human testing information tracking section.

The Chief Complaint section includes a Chief Complaint Category 1410, specific Chief Complaint field 1412, and an Add Chief Complaint Remarks button 1414. The Chief Complaint Category 1410 includes a dropdown menu that lists out a variety of possibilities as illustrated in FIG. 14(*b*). The Chief Complaint field 1412 also is completed using a dropdown menu, and that menu is illustrated in FIG. 14(*c*). The ICD9 code of the selected chief complaint is automatically stored in the background so that the encounter can be exported to other systems. The chief complaint remarks textbox 1414*a* shown in FIG. 14(*d*) is populated with a textual description of the selected complaint information and allows the user to add additional remarks based on the complaints stated by the patient. The Date of Onset field 1416 is for entry of the date the patient first noticed the symptoms leading to his/her complaint.

The Vital Signs section includes an Edit Vital Signs button which leads the user to the interface shown in FIG. 14(*e*) and a vital signs summary field 1420. The vital signs interface allows the user to enter whether the temperature, pulse, respiratory, and/or blood pressure are normal or abnormal. The exemplary embodiment is set up to set the vital signs summary to normal if all four vital signs are normal, otherwise if one of the vital signs is abnormal then the vital signs summary field 1420 will show abnormal as illustrated in FIG. 14(*f*).

The Physical Findings section includes an Edit Physical Findings button 1422 and physical findings summary field 1424. When the Edit Physical Findings button 1422 is clicked, the user is presented with an interface illustrated in FIG. 14(*g*). The physical characteristics being observed in this exemplary embodiment are the head, ear, nose and throat (HEENT); lungs; cardiovascular (CV); abdomen (ABD); musculoskeletal (MS); neurological (Neuro); and genitourinary (GU). The user decides if each of the physical characteristics is normal, abnormal, or N/A; and by default all of the findings are marked as N/A. If nothing is entered for physical findings, then the physical findings summary will be blank. If one or more physical findings are abnormal, then the physical findings summary read Abnormal similar to what is shown in FIG. 14(*h*). If all of the physical findings are normal, then the physical findings summary will read Normal.

The Differential Diagnosis section allows entry of a diagnosis by the user and/or verification of a proposed diagnosis based upon the entered complaints. The Affected System field 1426 is for entry of the system impacted by the complaint(s) of the patient and is a dropdown menu listing different body systems as illustrated in FIG. 14(*i*). The Diagnosis dropdown menu 1428 is populated with a list of possible diagnoses based on the selected affected system as illustrated in FIG. 14(*j*). Any number of diagnoses may be selected, which is also illustrated by the multiple highlights in FIG. 14(*j*). The ICD9 code for each of the diagnosis selected will automatically be saved with the encounter. The save codes will be displayed in a review presentation of the encounter. Additional information regarding the diagnosis can be entered in the Differential Diagnosis Remarks textbox 1430a in FIG. 14(*k*) activated by the "ok" button.

The Plan of Treatment section of the sick call interface includes a Plan list, the fibrin section 1236, an Add Treatment Remarks button, and an Add Disposition button 1440. The Plan list includes a variety of items that may be included as part of the treatment plan, and it allows for multiple selections to be made as part of the treatment plan. The Add Treatment Remarks button provides a textbox for entry of any remarks that the user feels would be pertinent regarding the proposed treatment plan. The Add Disposition button when clicked provides a disposition interface like that shown in FIG. 14(*l*) that allows entry of the disposition of the sick call similar to the disposition functionality present in the field medical card interface. Multiple items may be checked as these dispositions are not necessarily mutually exclusive.

The Add Remarks/Comments button 1442 provides a textbox (not shown) that allows the user to enter information relating to the problems in the diagnosis, treatment, etc. including possible problems that may yet arise.

FIG. 15 illustrates an alternative encounter form that may be accessed in the exemplary embodiment through the SF600 button 412 on the startup screen. This encounter form shares the patient name and social security fields 1202, 1204, the sick call type 1206, the Epidemiology Information button 1208, the provider section 1244, and the disposition section 1240 with the field medical card interface shown in FIG. 12(*a*). This encounter interface includes a vital signs section 1510 that includes, for example, temperature (Temp), pulse (Pulse), respiratory (Resp), systolic blood pressure (Blood Pres Sys), diastolic blood pressure (Dia), and a pulse oximetry reading (SPO2). The Subjective textbox 1512 and Objective textbox 1514 are for entry of their respective types of observations regarding the patient. The assessment section includes an Affected dropdown menu 1516 for the affected system (similar to the Affected System dropdown menu 1426) and a Differential dropdown menu 1518 for the differential diagnosis (similar to the Diagnosis dropdown menu 1428). The Plan textbox 1520 is for entry of the treatment plan for addressing the injury. The Disposition section 1522 is similar to the disposition section 1240.

FIG. 16 illustrates the exam selection interface that is displayed when the user clicks on the Exam button on the startup screen. The name and social security number fields 1202, 1204 are for the patient selected on the startup screen and are the same as on the field medical card interface. This interface provides connection to multiple examinations through the Glasgow Coma Scale button 1602, the Mini-Mental Status button 1604, the Color Blindness Test button 1606, the Pre-Deployment button 1608, and the Post-Deployment button 1610. Each of the examination screens will include the examination name as a title and the patient identifying information. Once a response is entered, the examinations advance automatically to the next question/task.

The Glasgow Coma Scale is an examination used to aid in predicting early outcomes from a head injury. An exemplary question for the examination is shown in FIG. 17(*a*). The base format for the question screens includes the examination question 1702, a listing of answers/options 1704, a back button 1706, a sign and save button 1708 for saving the examination, and a next button 1710. The back and next buttons 1706, 1710 are for moving through the questions of the examination. After the last question is responded to, the results are provided on a summary screen like that illustrated in FIG. 17(*b*).

Figure 18A:
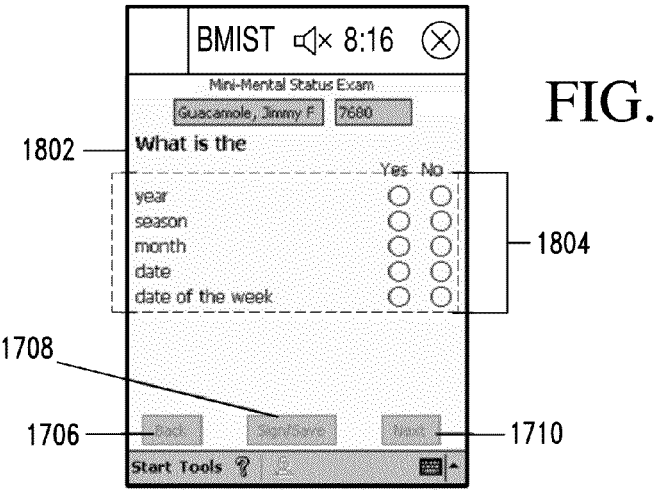
Figure 18B:
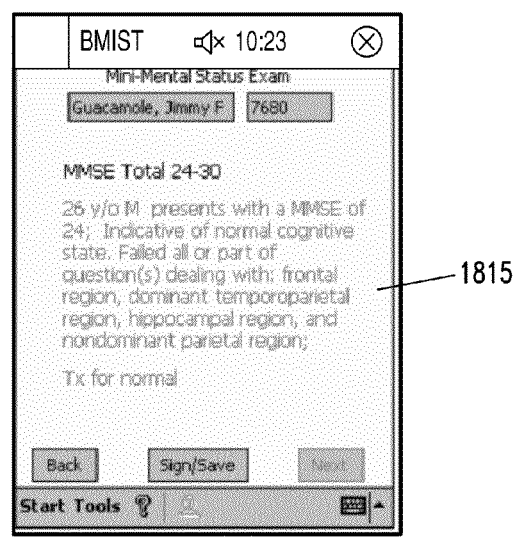

The Mini-Mental Status examination is used to evaluate the cognitive function of the patient. An exemplary question for the examination is shown in FIG. 18(*a*). The base format for the question screens includes the question or task description 1802 and the multiple choice response 1804 to the question or task. After the last question/task is completed and responded to, the results are provided on a summary screen like that illustrated in FIG. 18(*b*).

Figure 19A:
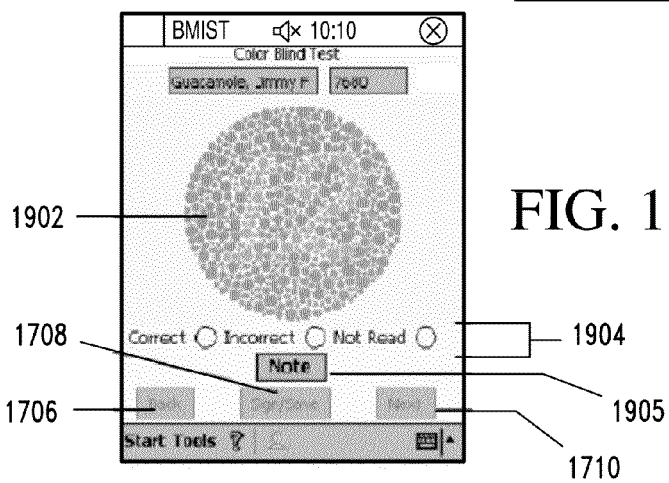
Figure 19B:
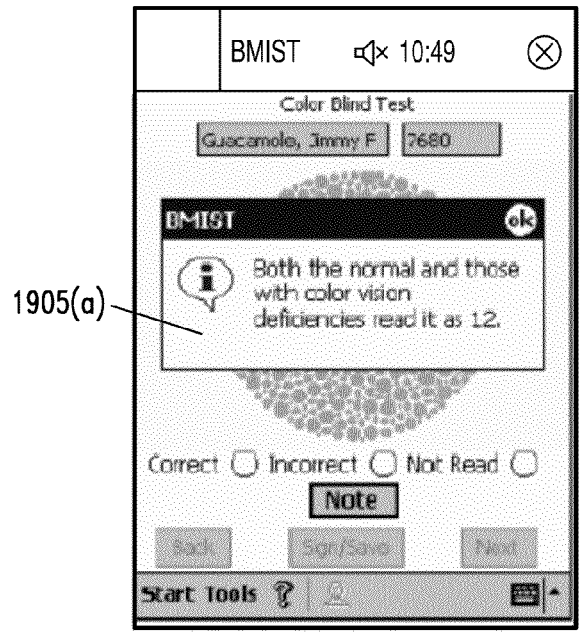
Figure 19C:
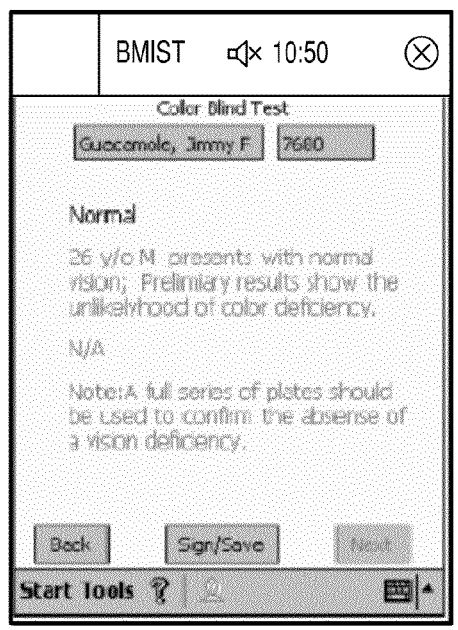

The Color Blindness Test is typically used to determine if the patient is colorblind. In the exemplary embodiment this test includes a series of six images to determine if the patient can see a number or not within the image. The base format for a slide screen includes the image 1902, a set of multiple choice answers 1904, and a Note button 1905, which provides information on how to interpret a patient impression of the image and a sample of a note is shown in FIG. 19(*b*). After the last slide is responded to, the results are provided on a summary screen like that illustrated in FIG. 19(*c*).

Figures 20, 21:
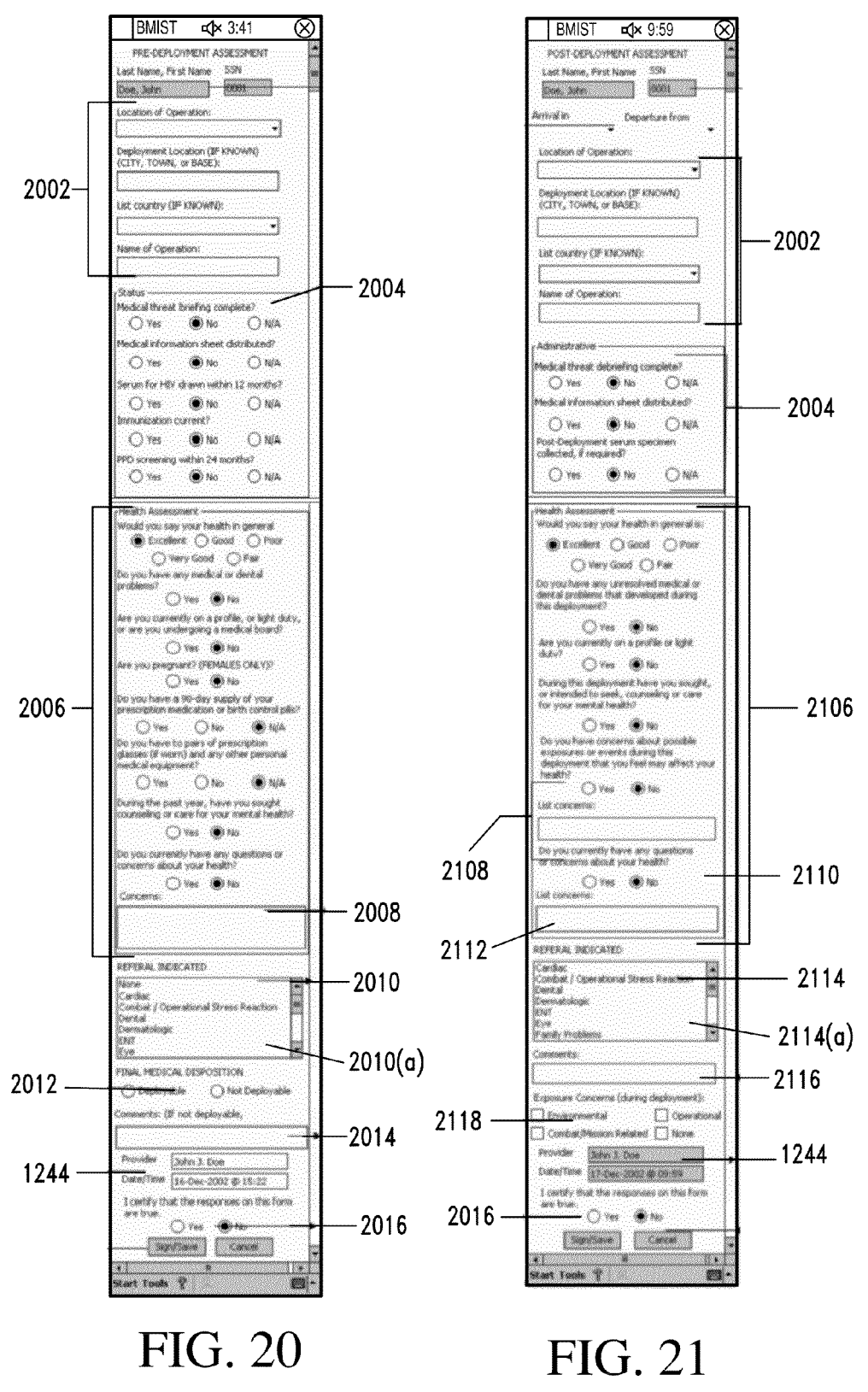

The Pre-deployment examination is for the deployed individual, who may later become a patient, to provide a base point regarding a variety of issues. FIG. 20 illustrates an interface for performing the pre-deployment examination. The location and operation information is entered if known and/or may be entered (due to secrecy issues) in the location and operation fields 2002. The individual is asked a series of questions 2004 providing the status of certain tasks being completed with the default being set to No. The next set of questions provides a health assessment 2006 of the individual (FIG. 20 shows the default settings for each of the questions). The individual also is asked if they have any concerns that should be noted in the record regarding their health. The next section is for possible referrals and includes a list of referral types 2010 from which the user can select including making multiple selections. The system makes a determination based on the entered information whether or not the individual should be deployed and notes its suggestion while allowing the user to overview the suggested determination in the final medical disposition 2012. If it is determined the individual is not deployable, then the user is provided comments and reasons as to why in the comments field 2014. The user also needs to certify that the responses are true 2016 before saving the information.

The Post-deployment examination is for after the individual returns from deployment to provide another base point regarding a variety of issues. FIG. 21 illustrates an interface for performing the post-deployment examination. The location and operation information is entered if known and/or may be entered (due to secrecy issues) in the location and operation fields 2002. The individual is asked a series of questions 2104 providing the status of certain tasks being completed with the default being set to No. The next set of questions provides a health assessment 2106 of the individual (FIG. 21 shows the default settings for each of the questions). The individual also is asked if they have any concerns regarding exposures or about their health in general 2106, 2110, and if so two respective text fields 2108, 2112 are provided for listing their concerns. The next section is for possible referrals and includes a list of referral types 2114 from which the user can select including making multiple selections. There is a text field 2116 for providing additional comments as to the referrals. The individual is asked whether they had any exposure concerns while they were deployed 2118 including environmental, combat/mission related, and operational. The user also needs to certify that the responses are true 2016 before saving the information.

Figures 22A, 22B, 22C:
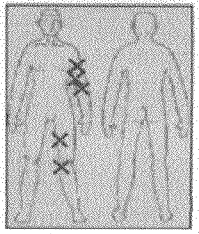
Figures 22D, 22E:
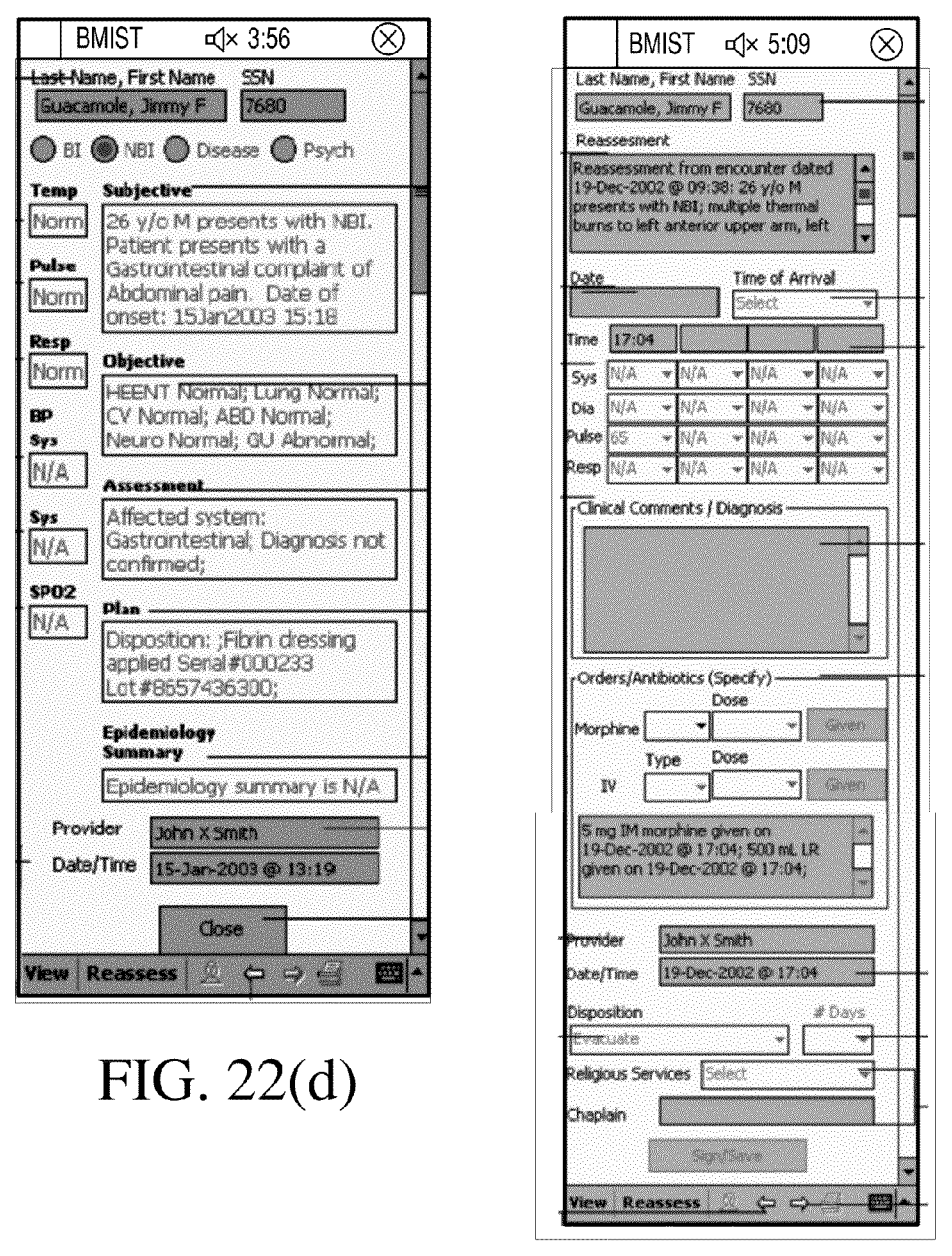
Figures 22F, 22G:
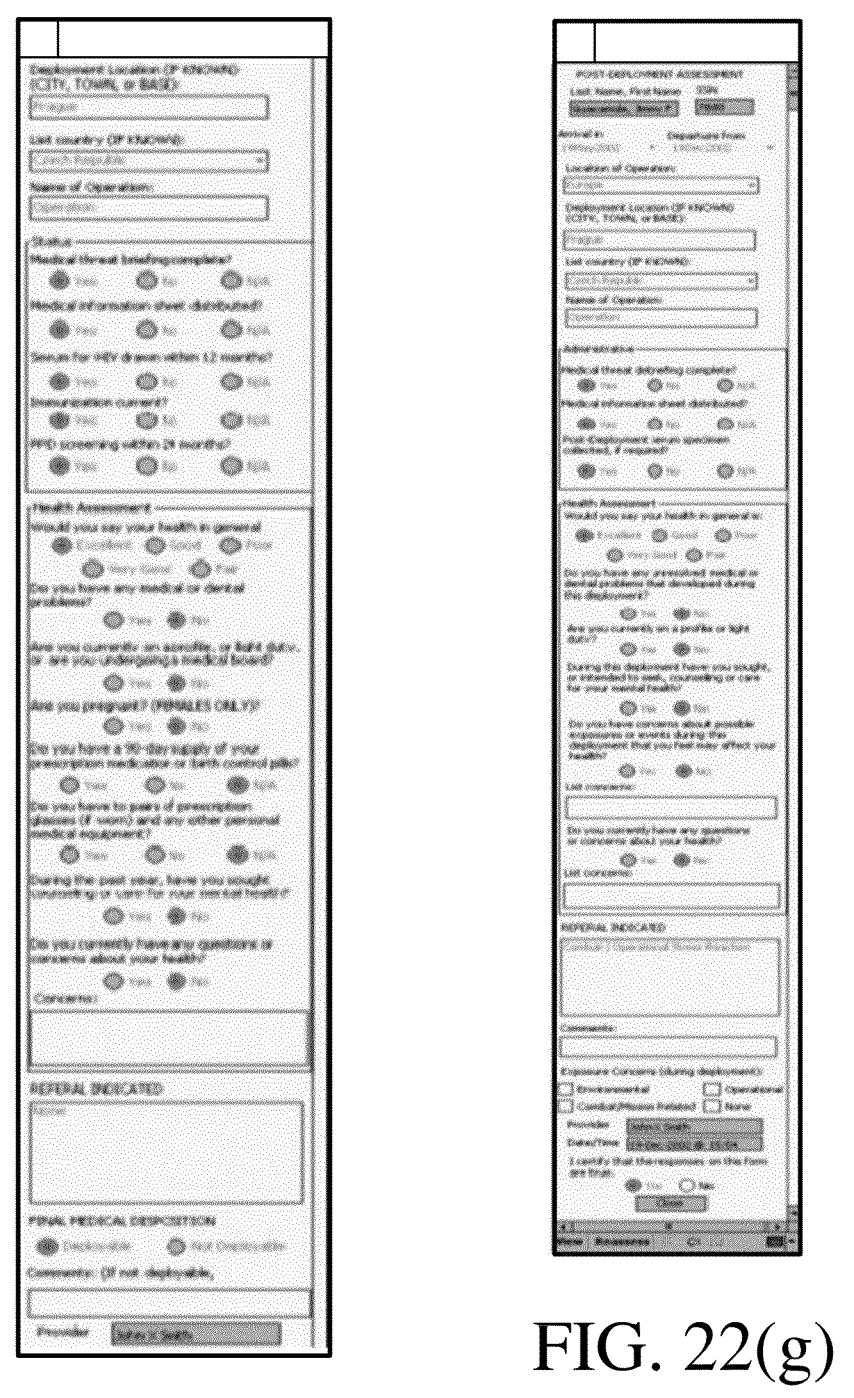

The exemplary embodiment also allows the review of prior encounters and examinations. FIGS. 22(*a*)-(*g*) illustrate the review capabilities of the exemplary embodiment. FIG. 22(*a*) illustrates the interface that is displayed after selecting a patient and when the Review button is selected on the startup screen shown in FIG. 4. The interface includes a listing 2202 of the encounters and examinations in the local database on the mobile computing device including the date, type, and summary for each encounter/examination. Once an encounter/examination is selected in the listing 2202, the user then can review the selection by clicking on the Review Encounter button 2204. If the user is finished reviewing past examinations/encounters for the patient, then by clicking the Close button 2206 the user will be returned to the startup interface.

FIG. 22(*b*) illustrates the field medical card form displayed as the alternative encounter form; however, the field medical card form may be displayed as it was entered as exemplified in FIG. 22(*b*) (expanded view menu) and FIG. 22(*c*). Both views have a Reassess button 2208 that when clicked will open a reassessment interface for entry of additional information. The arrow 2210 will return the user to the review encounter/examination interface shown in FIG. 22(*a*). FIG. 22(*d*) illustrates a sick call encounter displayed in the format of the alternative encounter type. FIG. 22(*e*) shows a reassessment that was reached by clicking on the forward arrow (will not be available if there is no reassessment) when the DD1380 encounter that led to the reassessment was displayed. FIGS. 22(*f*) and (*g*) illustrate the pre and post-deployment examinations in review form. Each of these past encounters and/or examinations are displayed in read-only form to prevent any changes being made.

Figures 23A, 23B:
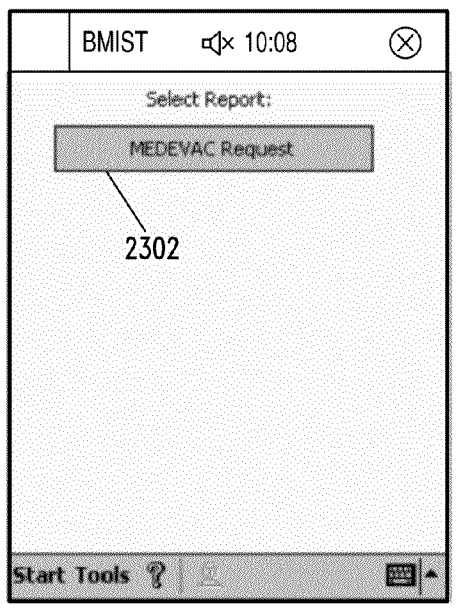
Figures 23C, 23D, 23E:
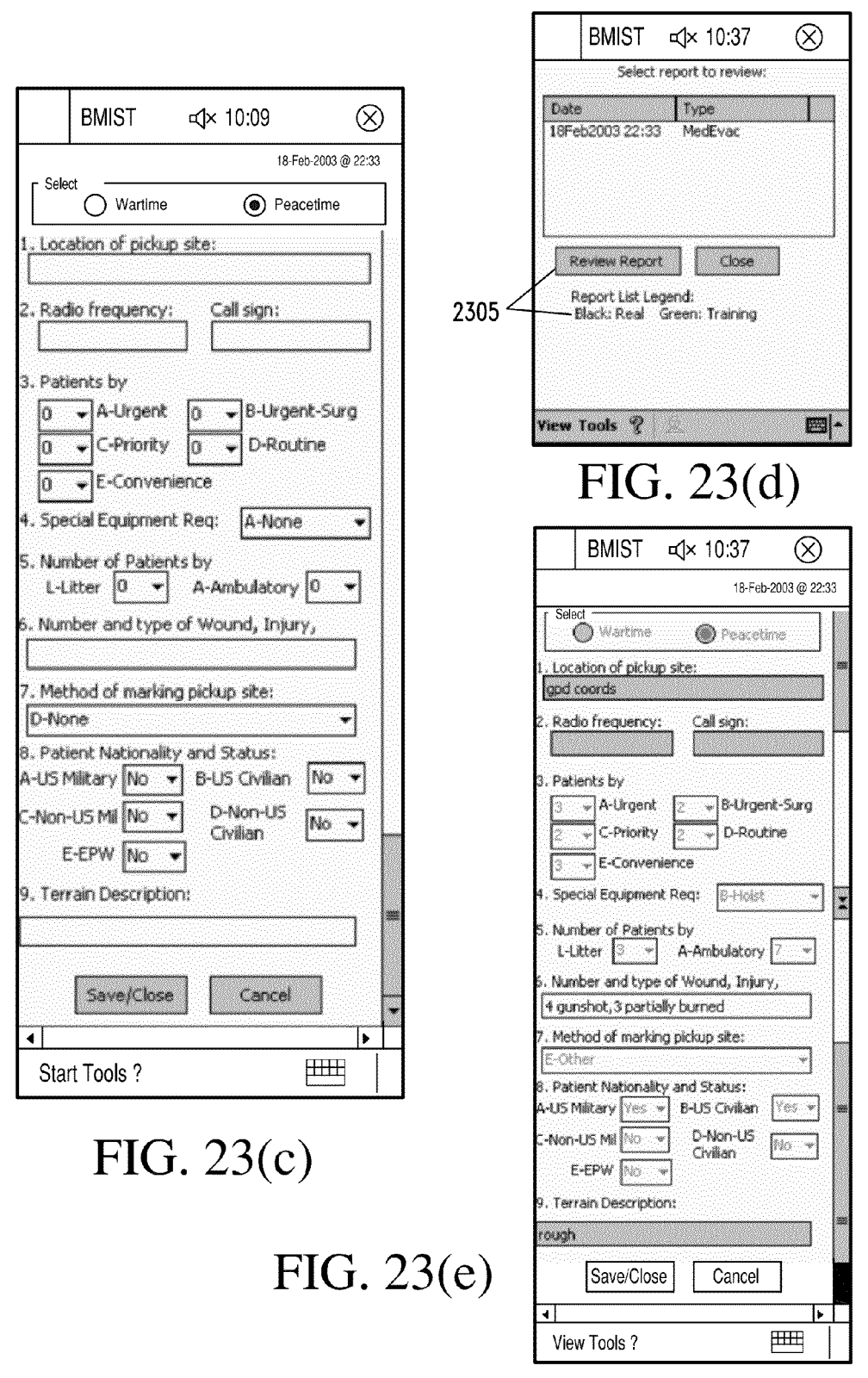

FIG. 23(*a*) illustrates a report interface that is reached by clicking on the Report button on the startup screen shown in FIG. 4. The exemplary embodiment only list one report, which is a MEDVAC Request (button 2302). FIGS. 23(*b*) and (*c*) illustrate a wartime MEDVAC Request and a peacetime MEDVAC Request, respectively. Depending upon where the mobile computing unit is, will dictate the availability of these two reports. FIG. 5(*a*) displays the Tools menu on the startup interface from which the user may review any previously created MEDVAC Requests. Upon requesting to review the MEDVAC Requests, the user is displayed the interface shown in FIG. 23(*d*) that lists out the requests that may be reviewed including the date and type. FIG. 23(*e*) illustrates a MEDVAC Requests shown in a reviewable read-only state.

FIG. 5(*a*) also shows that from the Tools menu, the user may access reference manuals to assist them in their health care duties.

Figure 24:
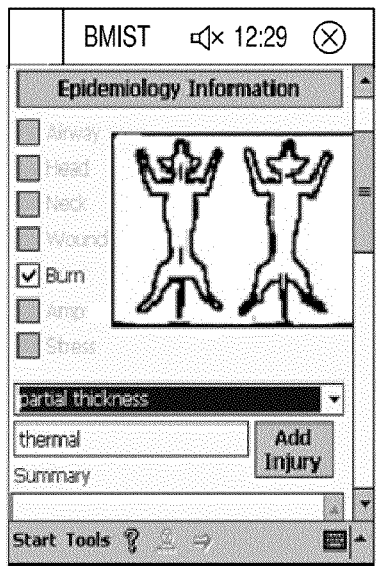
FIG. 24 illustrates an interface according to an exemplary embodiment according to the invention.
Figure 25A:
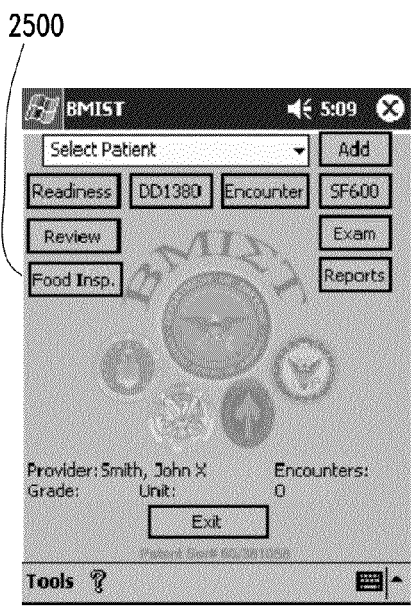
Figure 25B:
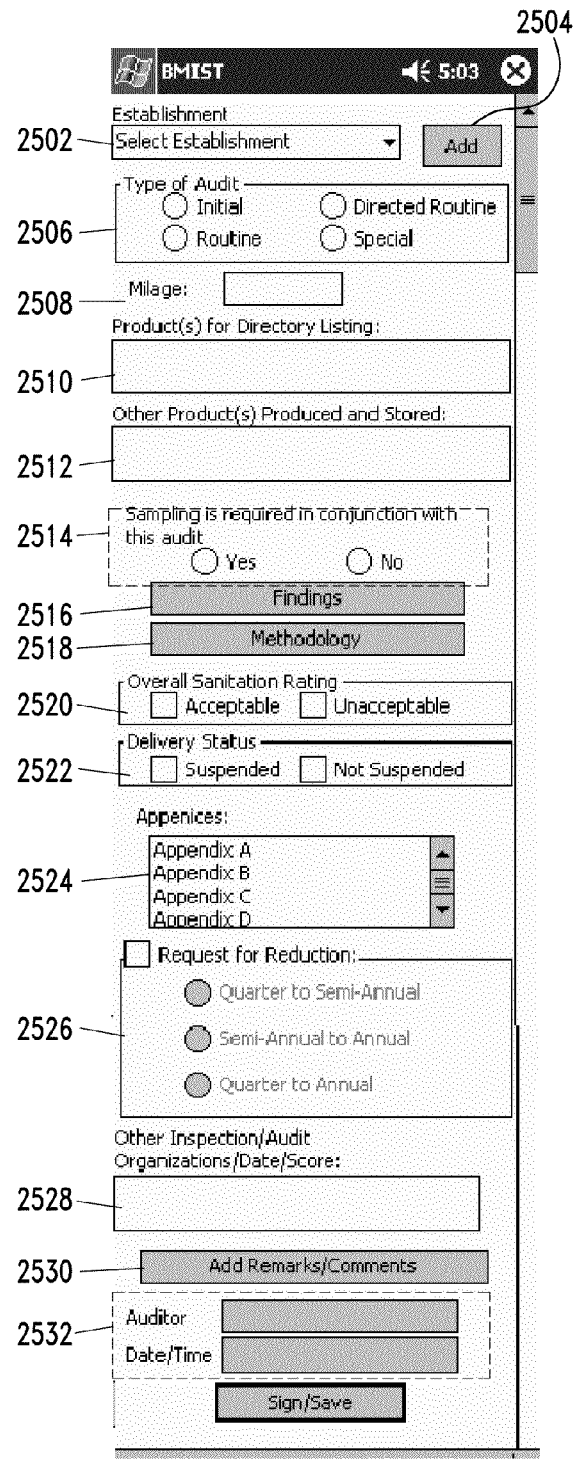
Figure 25C:
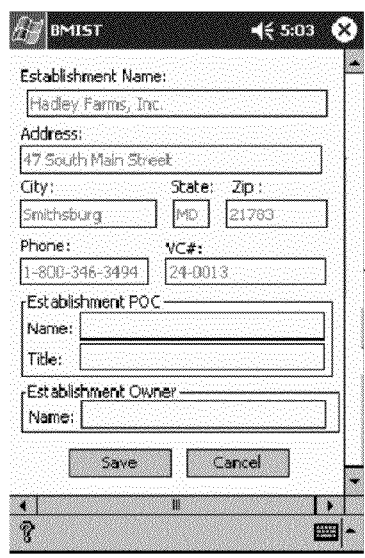
Figure 25E:
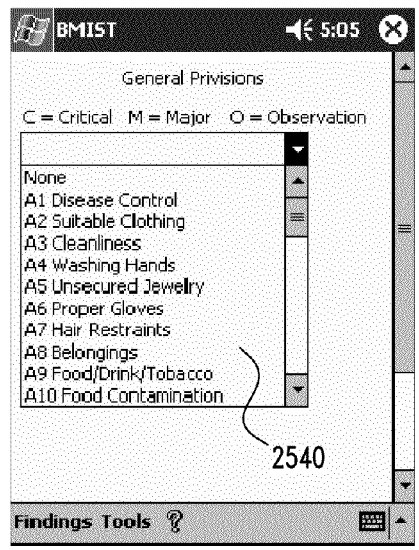
Figure 25D:
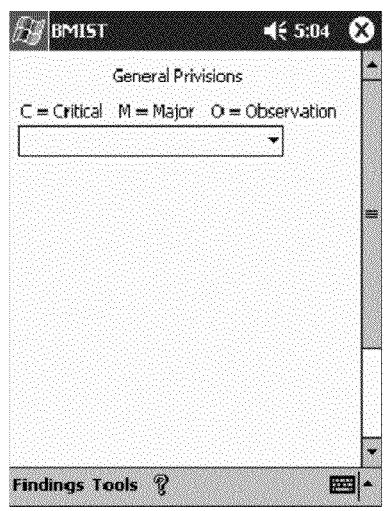
Figure 25F:
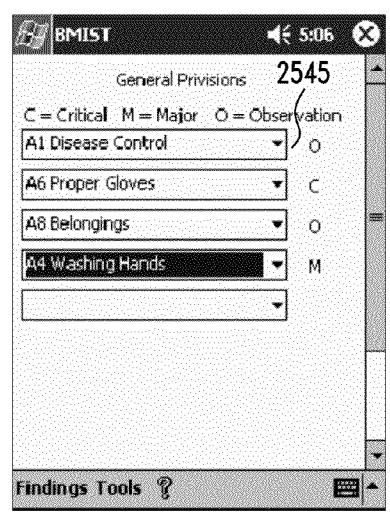
Figure 27A:
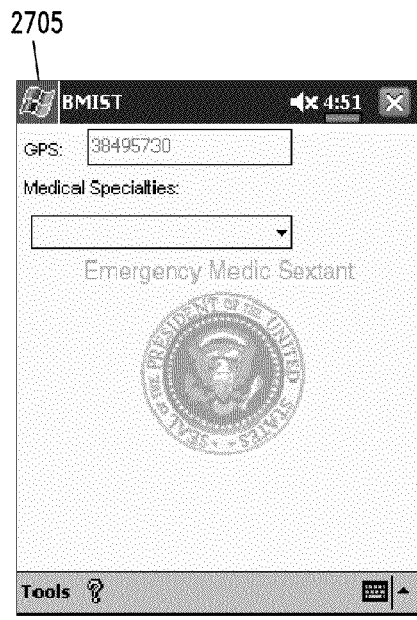
Figure 27C:
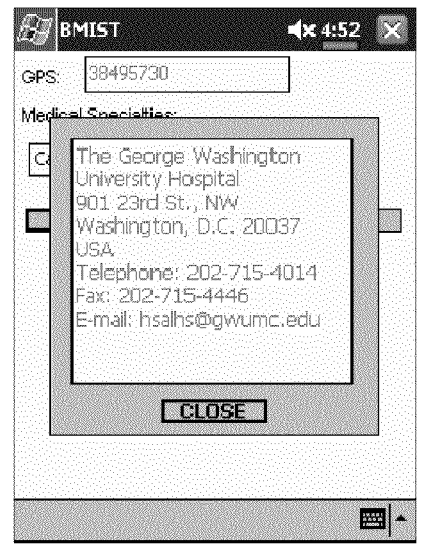
Figure 27B:
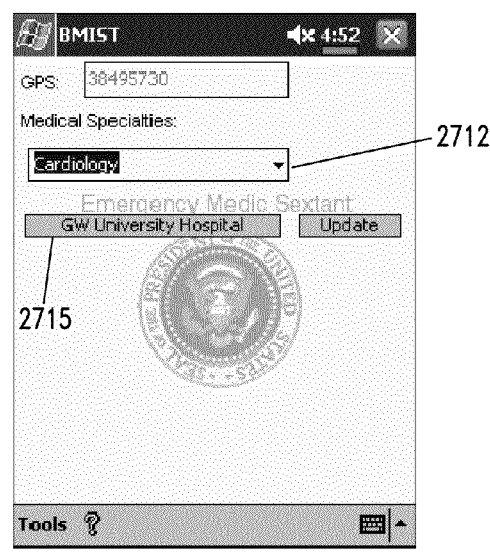
Figure 27D:
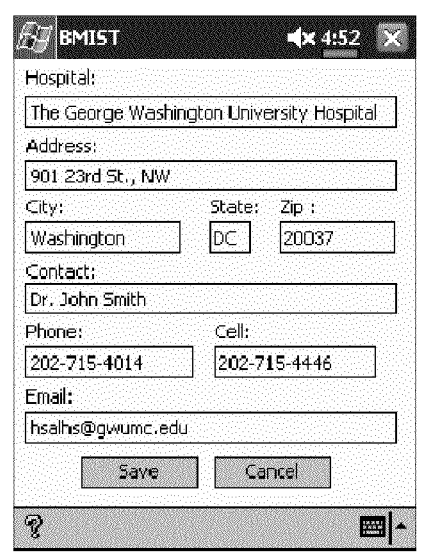

Another exemplary embodiment of the mobile computing device component is for application to the veterinary sciences and is similar to the above described exemplary embodiment with the primary changes being that the name fields is just one name field for the singular name of the animal and changing the human body figures to the appropriate animal (see FIG. 24 which illustrates a portion of form DD1380 for a dog). Other changes would include refining the available medications for the animal in which the interface is being designed. This aspect brings out an advantage to the system in that it is readily easy to change the data that populates the dropdown menus because the information is contained in XML files. In the case of the exemplary embodiment above, the data for the dropdown menus is assembled in a MS Excel spreadsheet and the data is pulled from the spreadsheet into a XML file.

An application of the invention is in food safety investigations of suppliers to the armed services although civilian health inspectors could find benefit in using this exemplary embodiment as illustrated in FIGS. 25(*a*)-25(*h*). This embodiment allows the inspector to document the conditions of the site including rating different components that make up the inspection. The inspector begins the process by selecting the Food Insep button 2500 on the startup screen shown in FIG. 25(*a*). Selection of the food inspection brings up the main inspection interface illustrated in FIG. 25(*b*). As with the patient embodiments discussed above, the inspector will select an establishment in the Establishment field 2504 or click on the Add button 2506 to display an interface to enter a new establishment. FIG. 25(*c*) illustrates an interface for adding an establishment into the database. The interface requests a variety of demographic information.

The inspector begins by selecting the type of audit to be conducted in the Type of Audit section 2506. The inspector may include any mileage required to reach the establishment in the mileage field 2508. The inspector also enters the products for inclusion in the directory in textbox 2510, which would be the products that the establishment is providing the armed forces, and other products that are produced and stored at the establishment in textbox 2512. The inspector indicates whether it will be necessary to sample any of the product in portion 2514 of the interface. The inspector clicks the Findings button 2516 to enter his/her findings regarding the establishment and the Methodology button 2518 to enter his/her methodology for the inspection. The inspector provides the overall sanitation rating in section 2520 and the delivery status in section 2522, although the system may be set to make a recommendations as to both of these based on the findings entered by the inspector. If there are any Appendices, then they are noted in section 2524. There is also a section to note any request to decrease the frequency of inspection in section 2526. If there are additional comments to be made, then a textbox can be accessed via clicking on the Add Remarks/Comments button 2530. The information regarding the inspector is automatically populated into the auditor section 2532 by the system.

FIGS. 25(*d*)-(*g*) illustrate different interfaces for use in this exemplary embodiment. FIG. 25(*d*) is the initial screen where the first finding is entered by the inspector by selecting from a dropdown list like that illustrated in FIG. 25(*e*). For each finding, the inspector enters whether the finding was critical (C), major (M), or observation (O), which can be used by the system in conjunction with the findings to provide a recommendation as to whether the establishment was sanitary and whether deliveries should be stopped. FIG. 25(*g*) illustrates an interface for entry the finding rating along with the general provision that relates to the finding in addition to having a textbox for supplying additional comments from the inspector. FIG. 25(*h*) illustrates the interface for explaining the methodology used by the inspector with different sections having their own textboxes. FIG. 25(*i*) illustrates an alternative interface that may be inserted between the startup screen and the audit interface if there are additional types of reports to be created that relate to food inspection.

A medical application of the invention is the use of the mobile computing device in performing behavioral analysis of soldiers. This embodiment provides a combat operational stress component for determining whether a soldier is fit to remain in the field and/or deployed. FIG. 26(*a*) illustrates an interface for entering information relating to a group meeting for discussion and/or educational purposes. The screen provides a list of questions and sections relating to demographic information about the attendees to provide a record of the extent of participation. At the bottom of the interface is information stating who lead the session along with the date and time of the session. FIG. 26(b) illustrates an interface to record a meeting with an individual that includes demographic information and includes space for laying out a treatment and/or action plan.

The invention also may be used in the preventive medicine field as an educational tool and a mechanism to insure that the deployed soldiers are healthy through periodic screening of their health.

Another medical application of the invention is in the research arena for tracking clinical studies and symptomatology related to the disease and/or infliction being studied. This embodiment has some similarity with the tracking of use of the fibrin bandage in the main exemplary embodiment, because in addition to tracking use the information relating to the injury being treated is being maintained to provide a fuller and complete medical record regarding what happened with the patients on who the fibrin bandage was used.

A modification of the exemplary embodiments and applications above of the invention is the incorporation of speech recognition into the mobile computing device to allow the user to talk his way through the screens in place of using a stylus or some other selection mechanism. Speech recognition includes both the oral verbalization and processing of larynx vibrations to develop a signal pattern and dictionary to enable the user to speak during use. The speech recognition component preferably would be implemented using software on the mobile computing device.

An add-on component to the system is a hospital locator that includes a database of hospitals (including contact information) and specialties correlated with GPS locations around the world. This add-on component alternatively could be packaged as a standalone item for PDAs and other mobile computing devices or central databases available to concierge-type services. The component would take the current GPS location of the individual along with the health issue (see FIG. 27(a)) and find the nearest medical facilities in the database along with the nearest medical facilities with the specialty to address the health issue (see FIG. 27(b)). The database may include additional contact information such as the doctors who head up the specialties (see FIGS. 27(c) and (d)) and information to enable the device providing directions on how to reach the medical facility. The interface shown in FIG. 27(d) also could be used for adding new medical facilities along with updating/editing information about existing medical facilities.

The invention in addition to having apparatus and system embodiments also includes methods for creating and capturing medical information. The above discussion regarding the exemplary embodiments and applications of the invention describe some methods for completing forms, gathering information, transferring information between devices/databases, and accessing data.

One exemplary method of using the system includes the initial setup of EICs and PDAs for use in the system, handling health situations, transmitting the medical information with the patient to the medical facility.

The initializing of EICs was discussed in detail as part of the primary exemplary embodiment. The method for initializing is shown in FIG. 28. First, in step 2805, the EIC is formatted to accept information and the formatting can be done using the mobile computing device with appropriate interface. In conjunction, before, or after the first step, the patient is setup in step 2810 as discussed above in connection with patient creation. The third step (2815) is to download the patient information onto the EIC. The next step (2820) is to provide the EIC to the individual for future use. Extensions of this method include downloading information gathered as part of pre-deployment processing in a military application and/or adding a medical history of the individual to the EIC.

The setup of the PDAs can be accomplished a variety of ways including the importing of information for individuals who would be cared for by the medical professional being assigned the PDA. The information contained on the EIC would mirror the imported information. Alternatively, the PDA could be setup to obtain all of its information on the fly from EIC and/or over a network. In any event the setup should be determined and performed prior to deployment of the PDA.

FIG. 29 illustrates a method according to the invention for handling medical information from the point of treatment back through treatment at a medical facility. The first step (2905) is to process the encounter for the medical situation as outlined in more detail in connection with the primary exemplary embodiment. After receiving the medical information, it is transferred to a database accessible at a medical facility through a network remotely, an EIC, or a network onsite with the database in step 2910. Preferably, the transfer in the military environment will occur with the medical information being transferred from the PDA of the medic to the EIC, and upon arrival at the medical facility a staff person will read information from the EIC and transfer that information to a database accessible at the medical facility from other staff members. In the civilian world, preferably the transfer will occur with transmission of the medical record over a wireless connection from the scene, in transit, or once on the grounds of the medical facility. As the patient is treated under either scenario, additional medical information is accumulated and attached to the patient's medical record (step 2915). The medical staff may also make use of the system with appropriate forms for entering the additional medical information via mobile computing devices. In the military environment, upon the patient leaving the medical facility, the patient's medical record is downloaded to the patient's EIC.

FIG. 30 illustrates a method for tracking the use of medical supplies by a medical professional or staff. Prior to performing the method, an inventory of supplies for the medical professional needs to be taken to know what is in the inventory. That information is preferably entered into the system either through an interface or as a XML file. In the first step (3005), the amount of a medical supply used in treating a patient, is decremented against the inventory. The second step (3010) is monitoring the inventory level of each type of supply to detect when an item goes below a predetermined threshold. When a threshold is reached, additional supplies of the item(s) that is low (3015) via the network. A notification is sent on an EIC, or the user is notified to pick-up additional supplies when he/she returns to a location where supplies may be obtained. An addition to this is the inclusion of the inventory tracking being accessed by the system intelligence in recommending treatments to new patients such that when an item runs out, an alternative treatment is suggested (3020), or when an item runs low that has an equivalent item in greater supply, the equivalent is suggested to be used for the treatment of the patient. A modification to this exemplary embodiment is that as part of the preparation stage, the system provides a list of items that should be present based upon the equipment and medical supplies that the medical professional should have for their position.

VI. Industrial Applicability

The present invention can serve as a model for civilian. These technical and clinical innovations in the development, training and support of deployed telemedicine operations greatly enhances the level of command, control, situational awareness, and overall health care delivery provided by the U.S. Army Medical Command during contingency type operations. This invention is capable of being an enabler of first-responder medical combat casualty care and forward health services in operations characterized by highly mobile, extended, nonlinear battlefields, with a minimum forward-deployed medical logistics footprint.

The invention provides Commanders with real time access to the readiness status of their troops and provides support for medical command and control, telemedicine and medical informatics applications across the continuum of the entire spectrum of military medical operations but especially for the first responder and far forward medical facilities. The invention also may be implemented to include complete support for sick call algorithms based on the first responders MOS. At the start of the mobile computing device, the available options may be preset to correspond to the user's MOS. Another exemplary embodiment provides for tracking medical supplies as they are used in treating patients. This type of information then can be used to formulate a treatment plan, because the system includes sufficient intelligence to know what supplies the medic has at the time of the encounter. The intelligence preferably maintains a running inventory by decrementing the number of supplies as they are being used. The system also will allow the medic to order new supplies using the mobile computing device or automatically once certain levels are reached.

I claim:

1. A method for receiving information from a user regarding an injury received by a patient comprising:
    receiving in a mobile computing device from the user through a graphical interface identification of the type of injury and classification of the injury,
    receiving from the user a location of the injury based on the user tapping at least one body part illustrated on a graphical representation of a body displayed on the mobile computing device where the mobile computing device receives a signal from a display of an area tapped by the user,
    receiving in the mobile computing device additional information from the user regarding the injury selected from a list that is based on the injury classification,
    populating an electronic medical record stored on the mobile computing device with the information received from the user regarding the injury where the mobile computing device populates the electronic medical record,
    creating and providing an injury summary for the patient's injury to the user based on the received information contained in the electronic medical record, where the mobile computing device creates and provides the injury summary,
    adding the injury summary to the electronic medical record stored on the mobile computing device,
    estimating a level of consciousness of the patient for the user based on the received information contained in the electronic medical record, where the mobile computing device estimates the level of consciousness of the patient and provides the estimated level of consciousness to the user,
    receiving in the mobile computing device confirmation of the estimated level of consciousness from the user after the level of consciousness is estimated,
    preparing and recommending a course of treatment to the user based on the information received from the user including at least one of the information used to create the injury summary, confirmed estimated level of consciousness, medications given to the patient, and vital sign information, where the mobile computing device prepares and recommends the course of treatment, and
    adding the estimated level of consciousness and the course of treatment to the electronic medical record stored on the mobile computing device.

2. The method according to claim 1, further comprising:
    receiving a request to update the electronic medical record from the user by the mobile computing device,
    displaying another interface on the mobile computing device for receiving information regarding the injury in response to the request,
    receiving additional information regarding the injury from the user via the displayed another interface, and
    adding the received additional information regarding the injury to the electronic medical record for the patient.

3. The method according to claim 1, further comprising:
    receiving identification of the patient from a removable computer readable medium, and
    copying at least a portion of the electronic medical record to the removable computer readable medium containing the identification of the patient.

4. The method according to claim 1, further comprising providing reference information upon request from the user.

5. The method according to claim 1, further comprising receiving epidemiology information regarding exposure to environmental conditions, radiation, chemical, or biological and whether other individuals have similar diagnosis or symptoms.

6. The method according to claim 1, further comprising:
    comparing diagnosis and symptom information for the patient against stored diagnosis and symptom information of other patients to determine whether there are any trends in injuries, and
    providing the trend analysis to the user.

7. The method according to claim 1, further comprising locating a medical facility equipped to address the injury based on the information received by the mobile computing device where locating is performed by a GPS means in cooperation with a database of medical facilities from which a selection is made.

8. The method according to claim 7, further comprising providing directions to the medical facility with the mobile computing device in cooperation with the GPS means.

9. The method according to claim 1, further comprising:
    receiving a request by the mobile computing device to update the information previously provided by the user,
    displaying another interface on a display for the mobile computing device for receiving information regarding the medical condition in response to the request, and
    receiving additional information into the mobile computing device regarding the medical condition via the another interface and adding the received information to the electronic medical record for the patient.

10. The method according to claim 1, further comprising:
    tracking at least one supply level by decreasing an inventory count by one when the course of treatment calls to use the supply being tracked; and
    altering the recommended course of treatment when the supply level goes below a predetermined threshold.

11. A computer program product for creation of an electronic medical record from a place remote from a medical facility, said computer program product comprising:

a computer readable storage medium having stored thereon:

first program instructions executable by a mobile computing device to cause the mobile computing device to receive in the mobile computing device from the user through a graphical interface identification of the type of injury and classification of the injury, second program instructions executable by a mobile computing device to cause the mobile computing device to receive from the user a location of the injury based on the user tapping at least one body part illustrated on a graphical representation of a body displayed on the mobile computing device where the mobile computing device receives a signal from a display of an area tapped by the user, third program instructions executable by a mobile computing device to cause the mobile computing device to receive in the mobile computing device additional information from the user regarding the injury selected from a list that is based on the injury classification, fourth program instructions executable by a mobile computing device to cause the mobile computing device to populate an electronic medical record stored on the mobile computing device with the information received from the user regarding the injury where the mobile computing device populates the electronic medical record, fifth program instructions executable by a mobile computing device to cause the mobile computing device to create and provide an injury summary for the patient's injury to the user based on the received information contained in the electronic medical record, where the mobile computing device creates and provides the injury summary, sixth program instructions executable by a mobile computing device to cause the mobile computing device to add the injury summary to the electronic medical record stored on the mobile computing device, seventh program instructions executable by a mobile computing device to cause the mobile computing device to estimate a level of consciousness of the patient for the user based on the received information contained in the electronic medical record, where the mobile computing device estimates the level of consciousness of the patient and provides the estimated level of consciousness to the user, eighth program instructions executable by a mobile computing device to cause the mobile computing device to receive in the mobile computing device confirmation of the estimated level of consciousness from the user after the level of consciousness is estimated, ninth program instructions executable by a mobile computing device to cause the mobile computing device to prepare and recommend a course of treatment to the user based on the information received from the user including at least one of the information used to create the injury summary, confirmed estimated level of consciousness, medications given to the patient, and vital sign information, where the mobile computing device prepares and recommends the course of treatment, and tenth program instructions executable by a mobile computing device to cause the mobile computing device to add the estimated level of consciousness and the course of treatment to the electronic medical record stored on the mobile computing device.

\* \* \* \* \*